(12) United States Patent
Floyd et al.

(10) Patent No.: US 12,178,541 B2
(45) Date of Patent: Dec. 31, 2024

(54) PROTECTIVE COVER INSTALLATION AND REMOVAL TOOL, SYSTEMS, AND METHODS

(71) Applicant: INTUITIVE SURGICAL OPERATIONS, INC., Sunnyvale, CA (US)

(72) Inventors: Paul J. Floyd, San Jose, CA (US); Rosemary Cole, Santa Clara, CA (US); Christina J. Shuh, San Francisco, CA (US); Ralph Wadensweiler, Sunnyvale, CA (US); Mark Palmer, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 897 days.

(21) Appl. No.: 17/179,670

(22) Filed: Feb. 19, 2021

(65) Prior Publication Data
US 2021/0259795 A1    Aug. 26, 2021

Related U.S. Application Data

(60) Provisional application No. 62/978,941, filed on Feb. 20, 2020.

(51) Int. Cl.
   *B25B 27/02* (2006.01)
   *A61B 34/35* (2016.01)
   (Continued)

(52) U.S. Cl.
   CPC .............. *A61B 46/17* (2016.02); *A61B 34/35* (2016.02); *B25B 27/02* (2013.01); *A61M 2005/3215* (2013.01)

(58) Field of Classification Search
   CPC .. A61M 2005/3215; B25B 27/06; B25B 9/02; Y10T 29/53657; Y10T 29/53683;
   (Continued)

(56) References Cited

U.S. PATENT DOCUMENTS 8,852,208 B2   10/2014  Gomez et al.
9,295,524 B2    3/2016  Schena et al.
(Continued)

FOREIGN PATENT DOCUMENTS

WO    WO-2018202458 A1 * 11/2018 .......... A61M 5/3202

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Tyrone V Hall, Jr.
(74) *Attorney, Agent, or Firm* — JONES ROBB, PLLC

(57) ABSTRACT

According to an exemplary aspect, a tool for installing and/or removing a protective cover of an instrument includes a body portion having an open end and a closed end. The open end defines an interior passage that extends into the body portion along a longitudinal axis of the body portion toward the closed end of the body portion. The interior passage is configured to receive at least a portion of the protective cover in the interior passage. One or more members are connected to the body portion, and each of the one or more members includes a free end movable relative to the body portion. Systems and methods relate to tools for installing and/or removing protective covers of instruments.

19 Claims, 21 Drawing Sheets

(51) Int. Cl.
*A61B 46/17* (2016.01)
*A61M 5/32* (2006.01)

(58) Field of Classification Search
CPC ............. Y10T 29/537; Y10T 29/53909; Y10T 29/53943; Y10T 29/53952
See application file for complete search history.

(56) References Cited

U.S. PATENT DOCUMENTS

| | | |
|---|---|---|
| 9,358,074 B2 | 6/2016 | Schena et al. |
| 10,039,594 B2 | 8/2018 | Krom et al. |
| 2012/0010611 A1* | 1/2012 | Krom .................... A61B 90/04 606/41 |
| 2014/0128886 A1 | 5/2014 | Holop et al. |
| 2018/0280625 A1* | 10/2018 | Cox .................... A61M 5/3204 |
| 2019/0015148 A1 | 1/2019 | Krom et al. |

\* cited by examiner

PROTECTIVE COVER INSTALLATION AND REMOVAL TOOL, SYSTEMS, AND METHODS

CROSS-REFERENCE TO RELATED APPLICATIONS

This application claims priority to U.S. Provisional Patent Application No. 62/978,941 (filed Feb. 20, 2020), titled "PROTECTIVE COVER INSTALLATION AND REMOVAL TOOL, SYSTEMS, AND METHODS," the entire contents of which are incorporated by reference herein.

TECHNICAL FIELD

Aspects of the present disclosure relate to tools for installing and removing protective covers for devices such as surgical instruments. Such tools include materials and configurations that facilitate ease of installing and removing protective covers while providing protection to the user from potentially hazardous instrument components.

INTRODUCTION

Various devices, such as surgical instruments, can be configured with multiple degrees of freedom of movement, such as articulation of joints, rotation of shafts, or other movements. Further, such instruments can include actuatable end effectors, such as jaws, clamps, forceps, staplers, and other devices. Components that provide such movement and functions are susceptible to contamination from fluids and material such as tissue during use in a working environment, such as during a surgical procedure. In addition, some instruments are configured to apply electrical current (e.g., electrosurgical energy) during a procedure, and various portions of the instrument may be required to be electrically insulated from the surrounding environment during such a procedure.

Some instruments include an electrically insulating protective cover that covers a distal end portion of the instrument while leaving the end effector exposed. It is desirable for the protective cover to be made at least partly from a flexible, resilient material, such as, for example, silicone rubber or other polymers. To reprocess such an instrument for reuse, the cover must be removed and the instrument components under the cover cleaned to ensure sterility. However, many materials otherwise suitable for the cover portion can potentially become slippery and difficult to grasp after exposure to or contact with fluids such as biofluids or materials such as living or necrotic tissue. In addition, many such instruments have a small diameter (e.g., <10 mm) and the small diameter potentially contributes to difficulties in removing the cover after use. Finally, such instruments can include sharp blades or pointed components that can potentially cause injury to a user attempting to remove a cover. A need exists for devices that facilitate installing and removing instrument protective covers in a safe and effective manner.

SUMMARY

Embodiments of the present disclosure may solve one or more of the above-mentioned problems and/or may demonstrate one or more of the above-mentioned desirable features. Other features and/or advantages may become apparent from the description that follows.

In accordance with at least one disclosed embodiment, a tool for installing and/or removing a protective cover of an instrument includes a body portion having an open end and a closed end. The open end defines an interior passage that extends into the body portion along a longitudinal axis of the body portion toward the closed end of the body portion. The interior passage is configured to receive at least a portion of the protective cover in the interior passage. One or more members are connected to the body portion, and each of the one or more members includes a free end movable relative to the body portion.

In accordance with at least another embodiment, a system includes an instrument with a distal end portion, a protective cover configured to be positioned over the distal end portion of the instrument, and a tool for one or both of installing and removing the protective cover from the instrument. The tool includes a body portion with an interior passage configured to receive the protective cover. The interior passage extends along a longitudinal axis of the body portion. The tool includes one or more members movable relative to the body portion, the one or more members each including an engaging portion configured to enter a junction between the protective cover and the distal end portion of the instrument when the protective cover is in an installed position on the instrument.

In accordance with yet another embodiment, a method of removing a protective cover from an instrument includes inserting a distal end of the instrument on which the protective cover is positioned within an opening of a tool; engaging an edge of the protective cover with a movable member of the tool; and while the edge is engaged, using relative movement between the instrument and the tool to remove the protective cover from the instrument.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1:
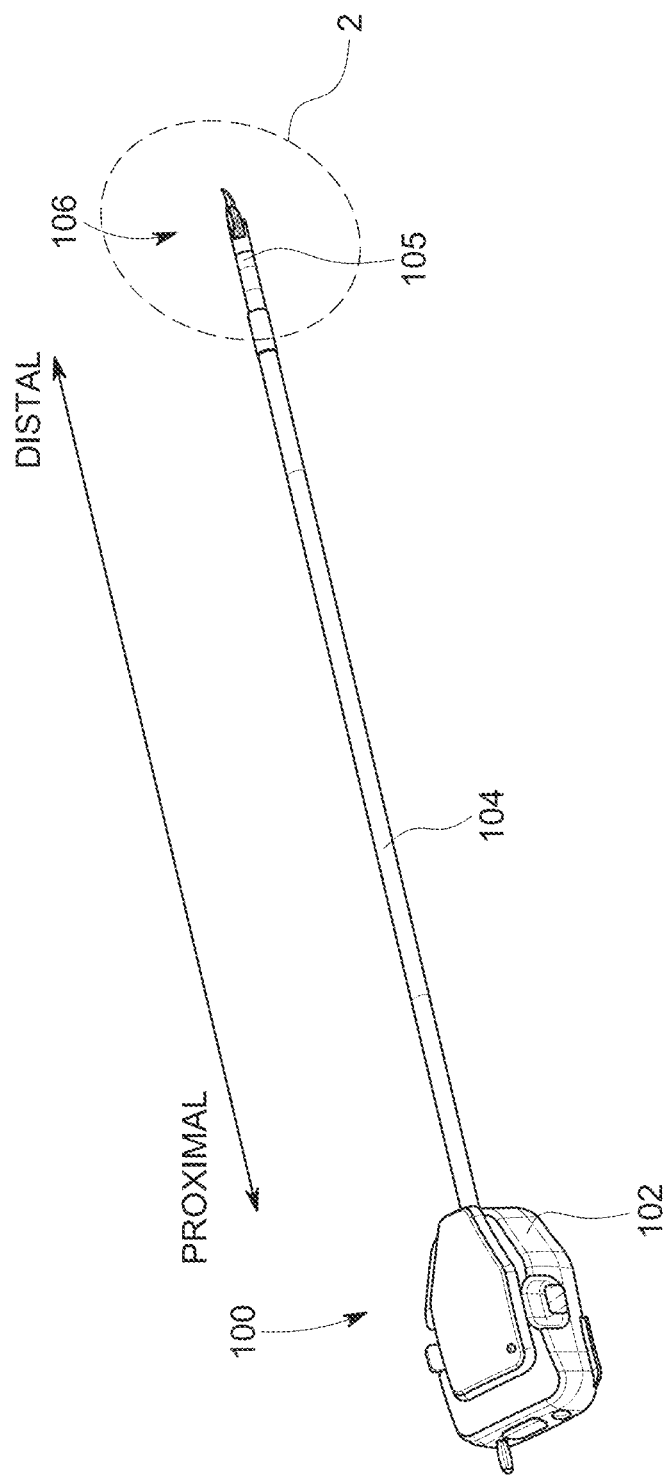
FIG. 1 is a perspective view of a surgical instrument according to the present disclosure.

The present disclosure discloses tools that facilitate installation and removal of protective covers on instruments. Such tools include features configured to assist a user in gripping the protective cover and preventing inadvertent contact between the user and an end effector of the instrument during installation of the protective cover over the instrument. The tools can also maintain sterility of the protective cover and the instrument as the tool is used to install the protective cover on the instrument. The tools include features configured to assist the user in separating and removing the protective cover from the instrument. For example, such tools can include a body portion with an interior passage shaped and dimensioned to receive a protective cover. The interior passage originates at an open end of the tool and extends along a longitudinal axis of the tool through the center of the tool and terminates at an at least partially closed end of the tool opposite the open end along the longitudinal axis. The interior passage is shaped and dimensioned to receive the protective cover and at least a portion of the end effector of the instrument.

The tool can optionally be provided to the user with a protective cover stored within the tool and ready for use, e.g., installation over an instrument. Alternatively, the tool can be provided separate from the protective cover and can be configured for multiple uses and sterilization between uses. The tool can optionally comprise multiple components assembled to form the body portion. Such configurations can facilitate manufacturability of the tool and facilitate the use of multiple types of materials in the tool as discussed further below.

The body portion can optionally include a protective cover engaging portion that is configured to engage a portion of the protective cover to facilitate removal of the protective cover from the instrument. The protective cover engaging portion can optionally include features configured to be manipulated by a user of the tool to engage the protective cover to assist in removal of the protective cover following a procedure. For example, a protective cover engaging portion can optionally include one or more members extending from the body portion and at least a portion of which is movable relative to the body portion. The one or more members can optionally be coupled with the body in a resiliently deformable manner. The one or more members can each include a wedge-shaped portion with a narrow end of the wedge-shaped portion facing radially inward.

The wedge-shaped portion is configured to facilitate removal of the protective cover by mechanical interaction between the wedge-shaped portion and a portion of the protective cover when the user manipulates the one or more members radially inward to bring the wedge-shaped portion into contact with the protective cover. Such manipulation can include, e.g., a user pinching or squeezing the one or more members to apply a radially inwardly directed force. The narrow end of the wedge-shaped portion can enter a junction between a portion of the instrument and the protective cover and engage (e.g., abut) a surface of the protective cover. While applying the radially inwardly directed force, the user can apply a longitudinal force to remove the protective cover by mechanical interaction between the protective cover and the wedge-shaped portion. For example, the wedge-shaped portion can engage (e.g., abut) an edge or end portion of the protective cover such that application of a longitudinal force pulls or slides the cover off the instrument. The longitudinal force can be accomplished by relative movement between the instrument and the cover installation and removal tool. For example, relative movement may include holding the cover in place while pulling the instrument away from the cover installation and removal tool, holding the instrument in place while pulling the installation and removal tool away from the instrument (in a direction along a longitudinal axis of the instrument), or a combination of the two.

The body portion can be formed of a single material, or optionally, may comprise multiple materials. For example, in some embodiments, the body portion includes a portion comprising a relatively rigid material that maintains shape under applied forces, and a relatively soft material on a surface of the relatively rigid material and within the interior passage. The relatively soft material can deform to provide an interference fit with the protective cover when the protective cover is inserted within the tool. The relatively soft material can optionally include one or more recessed portions on an inner surface of the interior passage. The body portion can also include a soft material forming an outer surface of the body portion, e.g., to enhance a user's grip on the body portion.

Referring now to FIG. 1, an embodiment of an instrument 100 (such as, for example, a surgical instrument) is shown. While aspects of the present disclosure are discussed in the context of surgical instruments, embodiments of the present disclosure can be used with various tools other than surgical instruments. The instrument 100 includes a force transmission mechanism 102 configured to interface with a manipulating system, such as manipulating systems shown and discussed in connection with FIG. 27 or 28, respectively. A shaft 104 extends distally from the force transmission mechanism 102. An end effector 106 is coupled to a distal end of the shaft 104. In some embodiments, the end effector 106 can optionally be coupled to the shaft 104 by one or more articulating joints 108 that provide one or more degrees of freedom of articulation of the end effector 106 relative to the shaft 104. In embodiments, operation of the end effector 106 and articulation of the one or more articulating joints 108 is controlled by the manipulating system (e.g., manipulating system 1000 or 1100) through the force transmission mechanism 102, which includes various mechanical and/or electromechanical devices that transmit motion, energy, and/or signals from the manipulating system to the end effector 106 and/or the one or more articulating joints 108.

In embodiments of the present disclosure, the end effector 106 can optionally comprise components such as articulatable joints, pivoting jaws, and other mechanical devices. Additionally, some tools include capability to apply electrosurgical energy through the end effector 106, such as to seal or cauterize tissue or for other procedures. In embodiments of the present disclosure, the distal end of the instrument 100 can include a protective cover (such as protective cover 210 shown in connection with FIG. 2; omitted from FIG. 1 for clarity) that prevents contamination of mechanical components of the instrument 100, reduces the potential for misapplication of electrical energy, and/or prevents contamination of the procedure site by the mechanical components. Such a protective cover is disclosed at least in U.S. Pat. No. 9,138,284 (filed Jun. 24, 2011) titled "ELECTROSURGICAL TOOL COVER," U.S. Pat. No. 10,039,594 (filed Aug. 24, 2015) titled "ELECTROSURGICAL TOOL COVER," and U.S. Patent App. Pub. No. US 2019/0015148A1 (filed Jul. 13, 2018), the entire contents of which are incorporated by reference herein. A protective cover is also briefly described below in connection with FIG. 2.

Figure 2:
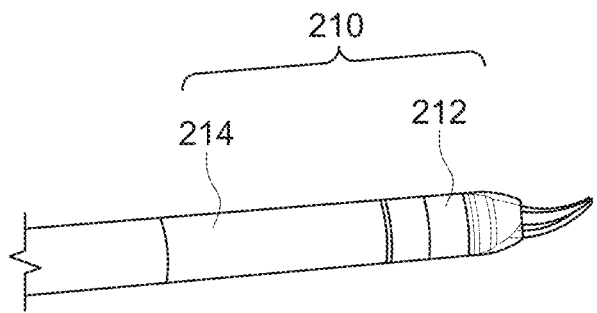
FIG. 2 is an enlarged view of a distal end of the surgical instrument of FIG. 1 with a protective cover installed.

Referring now to FIG. 2, an example protective cover 210 includes a distal portion 212 that can optionally comprise a relatively flexible material (such as, for example, a polymer such as silicone rubber) to cover moving components of the instrument 100, such as pivoting or articulating portions of the end effector 106. The distal portion 212 can optionally be bonded (e.g., adhered, welded, etc.) to a proximal portion 214 that comprises a material that is relatively stiffer than the material of the distal portion 212. Other examples of protective covers can optionally include more than two different materials, can include only a single material, or other combinations of components and materials. Such materials can include, without limitation, polymer materials such as thermoplastic polyurethanes, silicone-based polymers, and other materials.

The proximal portion 214 of the protective cover 210 can slide over a portion of the shaft 104 (FIG. 1) and the protective cover 210 is retained on the shaft 104 by an interference fit between the protective cover 210 and the shaft 104, such as an interference fit between the proximal portion 214 of the protective cover 210 and the shaft 104, an interference fit between the distal portion 212 of the protective cover 210 and the shaft 104, or both. Following a procedure, such as a surgical procedure, in which the instrument 100 is used, removal of the protective cover 210 can be required in order to effectively clean and/or sanitize portions of the instrument 100 for reuse. Due to the nature of the environment in which the instrument 100 can be used, for example, during a surgical procedure, various fluids and materials such as tissue present on the protective cover 210 after use can potentially make it difficult to remove the protective cover 210 from the instrument 100. For example, the protective cover 210 can become slippery and difficult to grasp, conditions which are exacerbated by the relatively small (generally <10 mm) outer dimensions of the protective cover 210. Additionally, in some instances, the end effector 106 can include components such as blades, points, etc. that could present a potential hazard to a user attempting to remove the protective cover 210 from the instrument 100.

Figure 3:
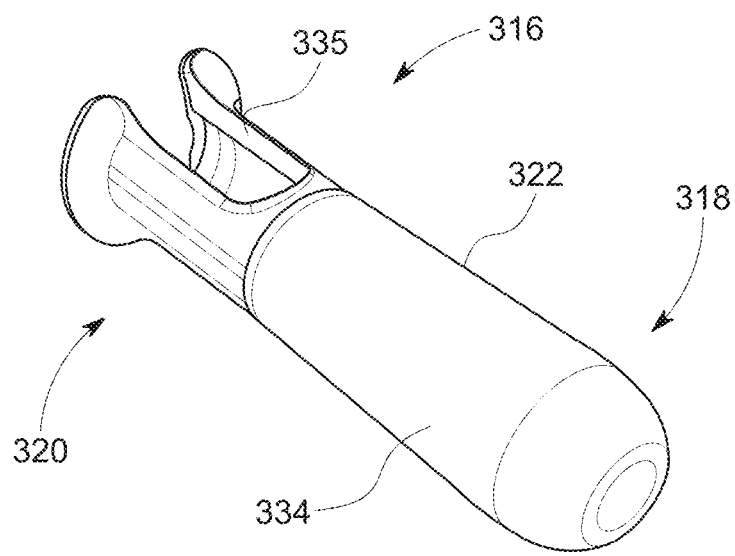
FIG. 3 is a perspective view of a protective cover installation and removal tool according to the present disclosure.
Figure 4:
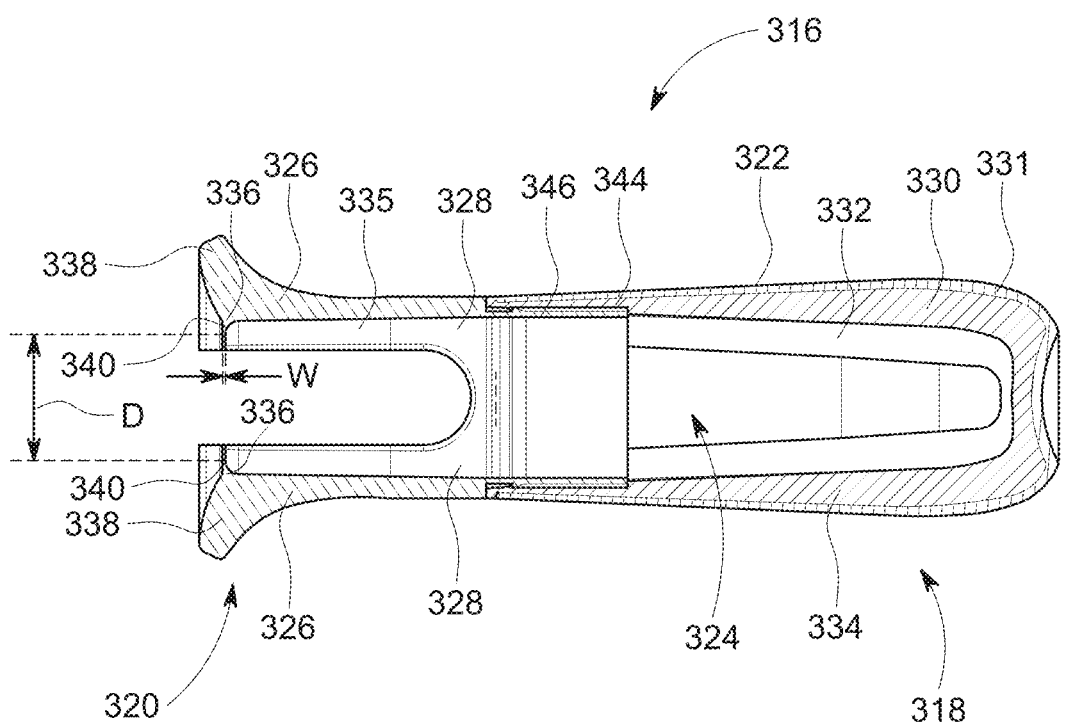
FIG. 4 is a cross-sectional view of the protective cover installation and removal tool of FIG. 3.

Embodiments of the present disclosure include devices (i.e., tools) configured to facilitate one or both of installation and removal of protective covers (such as protective cover 210) on or from the instrument 100. Referring now to FIGS. 3 and 4, a removal and installation tool 316 for installing and/or removing a protective cover is shown. The tool 316 includes a first end 318 and second end 320. In the embodiment of FIGS. 3 and 4, the first end 318 is generally enclosed and includes an outer surface 322 configured to be gripped by a user. The first end 318 includes an interior passage 324 (FIG. 4) configured to receive at least a portion of the protective cover 210.

The tool 316 can include multiple materials, each of which exhibits specific characteristics chosen to support various functional aspects of the tool 316. For example, in the embodiment of FIGS. 3 and 4, the first end 318 of the tool 316 includes a core portion 330 comprising a relatively rigid material, for example and without limitation, a polymer such as polyethylene, polypropylene, acrylonitrile butadiene styrene (ABS), or other polymers, metals or metal alloys, natural or composite materials, etc. The rigid material core portion 330 helps maintain shape of the tool 316 during use and enables the user to apply force to the tool 316 to operate the tool 316 as discussed below.

The first end 318 of the tool 316 can further comprise a resilient portion 332 within the interior passage 324. The resilient material insert 332 can comprise a material such as silicone rubber or another resilient polymer or other resilient material. The resilient material insert 332 can be configured to enhance retention of the protective cover 210 (FIG. 2) within the interior passage 324 by, e.g., a slight interference fit that requires mild deformation of the resilient material insert 332 as the protective cover 210 is inserted within the interior passage 324. Such an interference fit can serve to hold the protective cover 210 in place within the interior passage 324 as the protective cover 210 is prepared for installation or following removal from the instrument 100.

Optionally, the tool comprises a grasping area on a tool surface that includes a material to facilitate a user gripping the tool. For example, the tool optionally comprises a coating, sheath, or layer of one or more materials configured to improve the user's grip on the tool. Optionally, the first end 318 of the tool 316 includes a resilient material layer 331 on the exterior surface of the first end 318. The resilient material layer 331 can optionally comprise a polymer, such as silicone rubber or other material. The resilient material layer 331 can facilitate a user gripping the first end 318 and provide cushioning and tactile comfort to the user while the user operates the tool 316. In some embodiments, the tool does not include the resilient material layer 331, or can include other materials, such as hard polymers, to form the exterior surface of the first end 318.

The second end 320 comprises at least one member 326 extending away from the first end 318 and coupled with the first end 318 and movable relative to the first end 318. For example, in the embodiment of FIGS. 3 and 4, the second end 320 of the tool 316 includes first and second members 326 on opposite sides of the interior passage 324. The first and second members 326 are coupled to the first end 318 of the tool in a flexible manner such that the first and second members 326 can move, flex, or bend with respect to the first end 318 of the tool. For example, in the embodiment of FIGS. 3 and 4, the first and second members 326 are coupled with the first end 318 of the tool 316 in a flexible manner by a living hinge portion (e.g., resilient hinge portion) 328 of the second end 320. In other embodiments, the first and second members can optionally be coupled with the first end 318 of the tool 316 by a pivoting device, such as a pivoting hinge, or other mechanical structure. The second end 320 can comprise the same material as the core portion 330. While the material of the second end 320 and the core portion 330 can be referred to as a "rigid" or relatively rigid material, the geometry of the second end 320 can nevertheless be configured to permit flexing of the first and second members 326 relative to other portions of the second end 320 as well as the first end 318.

The first and second members 326 each include inwardly-extending radial projections. For example, in the embodiment of FIGS. 3 and 4, the first and second members 326 each comprise an inwardly tapering portion that forms, for example, a wedge-shaped projection portion 336 proximate free ends 338 of the first and second members 326. The wedge portion 336 includes a narrow end 340 facing radially inward which gradually tapers wider toward a base portion 342 of the wedge portion 336. In the embodiment of FIGS. 3 and 4, the narrow ends 340 face one another across a central axis of the tool 316. In a relaxed state of the members 326 (i.e., with no force applied to the members 326), a distance D between the narrow ends 340 is greater than an outer diameter of the protective cover 210, thereby allowing the protective cover 210 to be inserted within the interior passage 324 of the tool 316.

In embodiments of the present disclosure, the narrow end 340 comprises a width W. The width W of the narrow end 340 can be, for example, in a range of from about 0.001 inch (0.0254 mm) to 0.050 inch (1.27 mm). In an embodiment of the present disclosure, the width W of the narrow end 340 is about 0.015 inch (0.381 mm). The width W of the narrow end 340 can be based on considerations such as being wide enough to exhibit sufficient durability for reuse and being narrow enough to enter and widen a junction between the protective cover 210 and a portion of the instrument shaft 104, as discussed further below in connection with FIG. 6, allowing the wedge-shaped projection portions to be used as pincer elements in a pincer-type movement.

In some embodiments, the tool 316 comprises multiple pieces that are assembled to form the tool 316. For example, in the embodiment of FIGS. 3 and 4, the first end 318 and second end 320 generally correspond with a first portion 334 and a second portion 335 that can be assembled together to form the tool 316. The first portion 334 includes a receiving portion 344 configured to receive a portion of the second portion 335. For example, in the embodiment of FIGS. 3 and 4, the first portion 334 receiving portion 344 comprises a cylindrical bore dimensioned to receive extension 346 of the second portion 335. In the embodiment of FIGS. 3 and 4, the extension 346 is cylindrical and comprises an interference fit with the receiving portion 344. The two-piece configuration shown in connection with FIGS. 3 and 4 can facilitate manufacturing of the tool 316. For example, such two-piece construction can potentially simplify required tooling (such as molds) for manufacturing the tool 316. In other embodiments, the tool 316 can optionally be a single piece, such as an integrally molded single piece, comprise multiple pieces bonded (e.g., glued or welded) together, or other configurations.

Figure 5A:
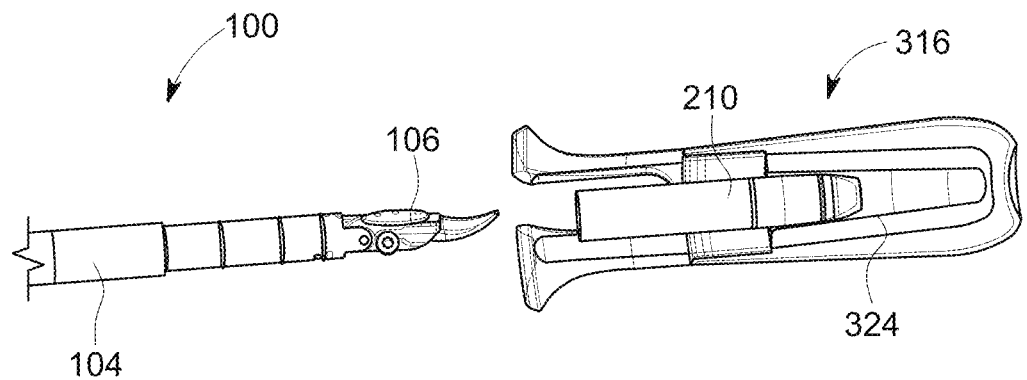
FIGS. 5A-5G show a sequence of installing and subsequently removing a protective cover using the protective cover installation and removal tool of FIG. 3.
Figure 5B:
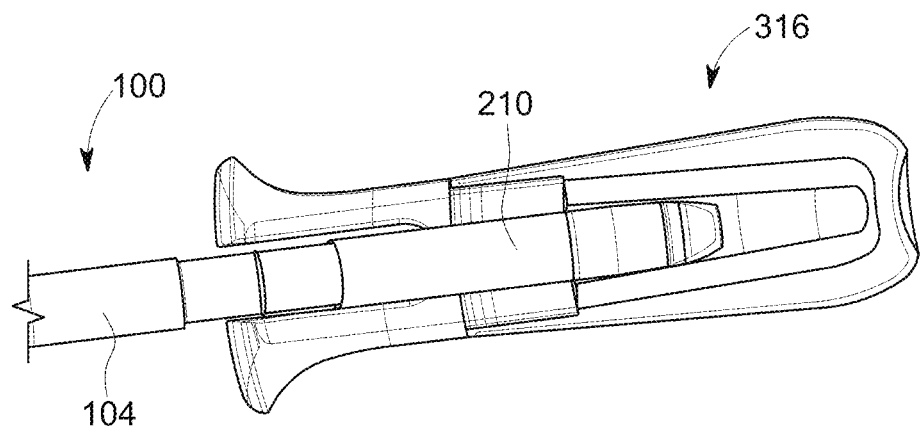
Figure 5C:
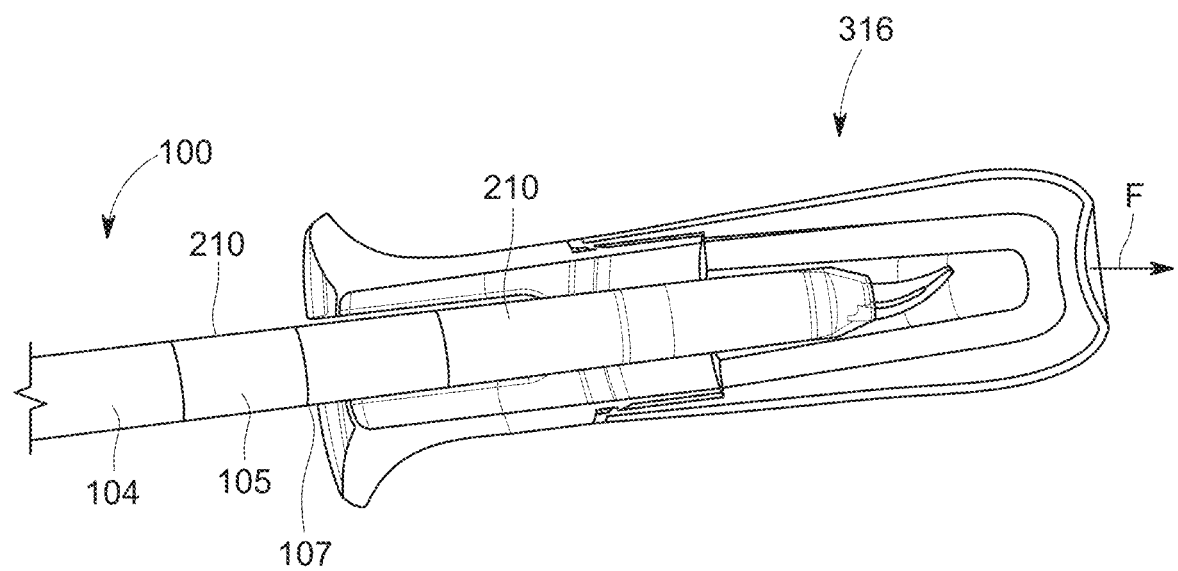

Referring now to FIGS. 5A-5G, function of the tool 316 is explained by way of an exemplary sequence of installing a protective cover 210 on an instrument 100 and subsequently removing the protective cover 210 from the instrument 100. Referring now to FIG. 5A, the instrument 100 without the protective cover 210 installed is shown. The protective cover 210 is held within the tool 316 and brought toward the end effector 106 of the instrument 100. In some embodiments, the protective cover 210 can optionally be pre-placed within the tool 316 as provided to the user; in other embodiments, the user is provided with the protective cover 210 and the tool 316 and must insert the protective cover 210 within the interior passage 324 of the tool 316. The protective cover 210, while held within the cavity/opening of tool 316, is placed over the end effector 106 and the user pushes tool 316 onto end effector 106 to position the protective cover 210 over the end effector 106 and over the shaft 104, as shown in FIG. 5B. Referring now to FIG. 5C, the user continues to advance the protective cover 210 over the end effector 106 and shaft 104 by pushing the tool 316 until the protective cover 210 is fully installed on the instrument 100.

In the embodiment of FIGS. 5A-5G, the shaft 104 includes an exterior cover portion 105 that can optionally comprise a size and material similar to the proximal portion 214 (FIG. 2) of the protective cover 210. Thus, when the protective cover 210 is fully installed on the shaft 104, a proximal surface 548 (FIG. 5F) of the proximal portion 214 of the protective cover 210 abuts the exterior cover portion 105, resulting in a nearly-smooth exterior surface with only a junction 107 between the outer surface of the protective cover 210 and the exterior cover portion 105.

Figure 5D:
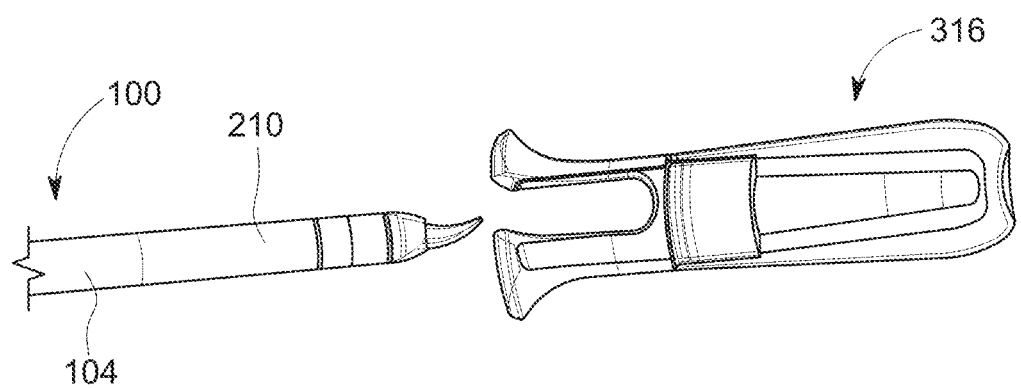

The tool 316 is then removed from the protective cover 210 and instrument 100 by the user pulling the tool 316 away from the instrument 100 and removing the tool 316 from the protective cover. For example, the tool 316 can be configured such that the interference fit of the protective cover 210 within the interior passage 324 of the tool 316 maintains a lesser hold on the protective cover 210 relative to an interference fit between the protective cover 210 and the shaft 104. With such an arrangement, once the protective cover 210 is fully installed on the shaft 104 as shown in FIG. 5C, when the tool 316 is pulled away from the distal end of the instrument 100, the protective cover 210 remains on the instrument 100, as shown in FIG. 5D. With the protective cover 210 in place, the instrument 100 can be used for a procedure, such as a surgical procedure.

Figure 5E:
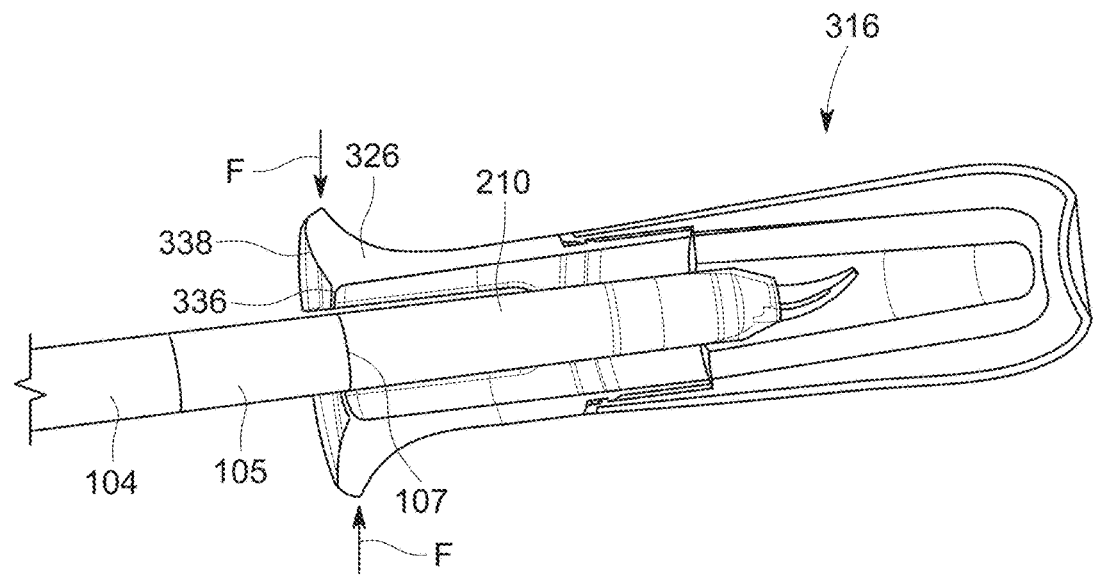
Figure 5F:
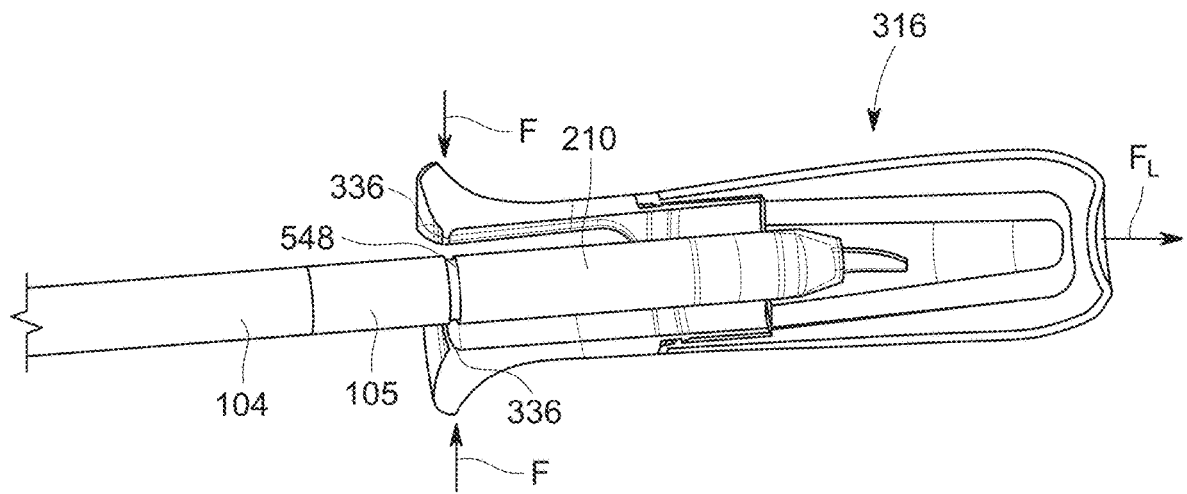
Figure 5G:
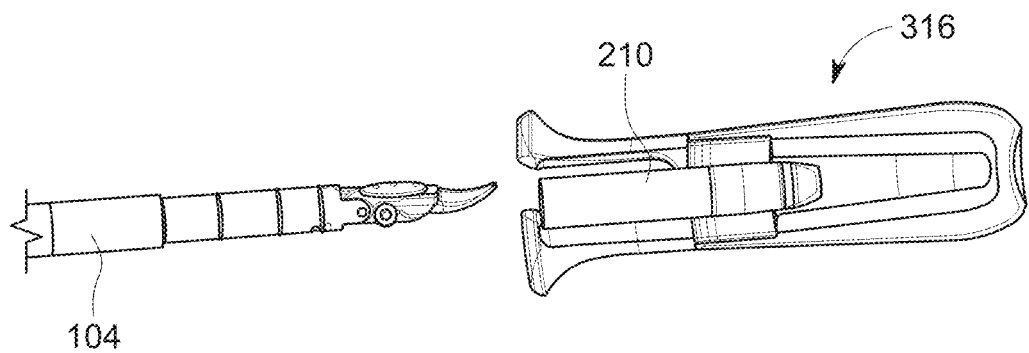

Following the procedure, removal of the protective cover 210 can facilitate cleaning of the instrument 100 for reuse. However, as discussed above, fluids and/or materials such as tissue remaining on the protective cover 210, as well as the relatively small outer diameter of the protective cover 210, can contribute to difficulty in removing the protective cover 210 from the instrument 100. Referring now to FIG. 5E, the protective cover 210 can be removed from the instrument 100 using the tool 316. The tool 316 is again placed over the protective cover 210 such that the protective cover 210 is located within the interior passage of the tool 316. The user then engages an edge of the protective cover 210 with a movable member of the tool 316 and using relative movement between the instrument 100 and the tool 316, removes the protective cover from the instrument. For example, in the embodiment of FIG. 5E, the user applies a radially inwardly directed force F to the members 326 (e.g., the user pinches or squeezes the members 326) of the tool 316. As a result, the free ends 338 of the members 326 flex radially inwardly and contact the surface of the shaft 104, and the wedge portions 336 abut the protective cover 210 at the junction 107 between the installed protective cover 210 and the exterior cover portion 105. As the user continues to pinch the members 326, the user pulls the tool 316 and protective cover 210 together from the instrument shaft 104 by applying a longitudinally-directed force $F_L$, as shown in FIG. 5F. Contact between the wedge portions 336 and the protective cover 210 pulls the protective cover 210 from the shaft 104 by overcoming the interference fit between the protective cover 210 and the shaft 104. The protective cover 210 can be fully removed from the shaft 104, as shown in FIG. 5G, and the instrument 100 is ready to be reprocessed (e.g., cleaned) and reused.

As the free ends 338 of the members 326 flex inward in response to the radially inwardly directed force F, the orientation of the free ends 338 of the members 326, and the wedge portions 336 located at the free ends 338, changes to some degree as a result. In other words, the force F applied to free ends of the members 326 results in a rotational movement of the free ends 338 about the base of the members 326 (i.e., the location at which the members 326 are coupled to the second portion 335 of the tool 316). As a result, the orientation of the wedge portions 336 can change relative to the shaft 104. Accordingly, in some exemplary embodiments, the particular shape and inclination of the wedge portions 336 can optionally be configured such that the wedge portions 336 exhibit the desired orientation for engaging the protective cover 210 when the members 326 are in the inwardly flexed position under force F.

Figure 6:
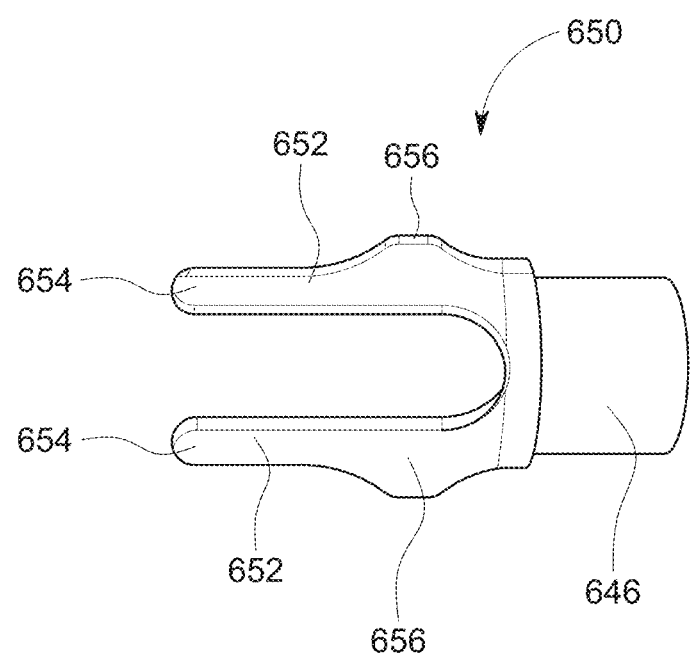
FIG. 6 is a side view of a portion of a protective cover installation and removal tool according to the disclosure.
Figure 7:
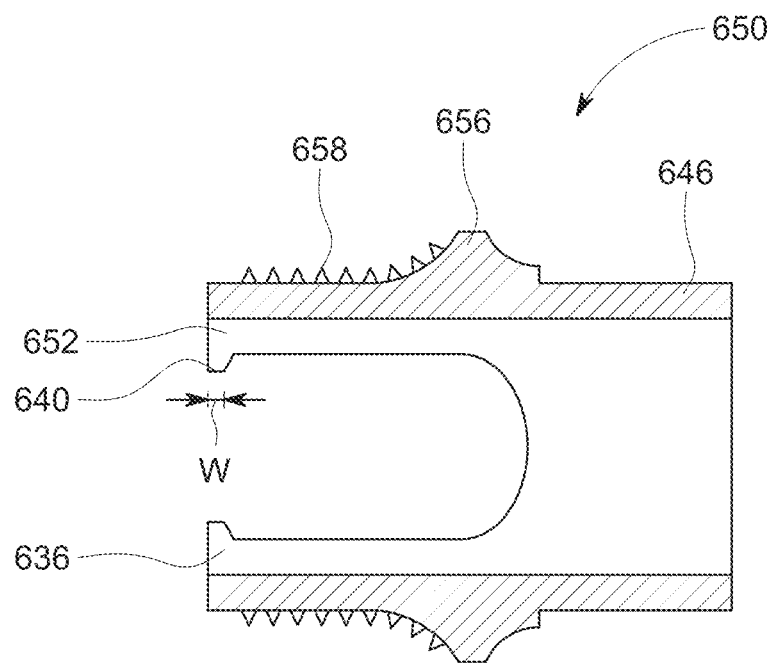
FIG. 7 is a cross-sectional view of a portion of a protective cover installation and removal tool according to the present disclosure.

Various features of the tool 316 can be configured to facilitate intuitive operation of the tool 316. For example, in the embodiments shown in FIGS. 3-5G, the members 326 are generally flared outward at free ends 338. In some embodiments, the shape of the members 326 can be configured to impart information regarding the operation of the tool 316 to the user. For example, referring now to FIGS. 6 and 7, an embodiment of a second portion 650 of a tool according to the present disclosure is shown in side view (FIG. 6) and cross section (FIG. 7). The second portion 650 of the tool can, for example, be used with the first portion 334 substantially as shown and described in connection with FIGS. 3-5G. The second portion 650 can optionally include a cylindrical extension 646 that interfaces with a first portion (e.g., first portion 334 in FIG. 3) in substantially the same manner as the second portion 335, i.e., the cylindrical extension 646 can be inserted within the receiving portion 344 of the first portion 334 (FIG. 3) to assemble the tool.

The second portion 650 can comprise two members 652 with free ends 654. The second portion 650 includes shoulder portions 656 opposite the free ends 654. A user can engage their fingers (such as thumb and forefinger) against the shoulder portions 656 when pinching the members 652 to catch and remove the protective cover 210, substantially as discussed above in connection with the embodiment of FIGS. 3-5G. The shoulder portions 656 can indicate to the user how to place their fingers to pinch the members 652, and the positioning of the shoulder portions 656 can facilitate the user in applying force to remove the protective cover 210 while pinching the members 652 by providing a surface against which the user can apply force in the correct direction.

The shoulder portions 656 and other areas of the members 652 can comprise a textured outer surface to increase friction between the user's fingers and the members 652 to further facilitate removal of the protective cover 210. In various embodiments, the textured surface can include, without limitation, grooves, ridges, cross-hatch patterns, a pebbled texture, such as a pattern of generally circular raised bumps, or other textures or combinations. In the embodiment of FIGS. 6 and 7, the members 652 include ridges 658 extending laterally across the surface of the members 652. The particular pattern of the texture can be chosen based on human factors, such as tactile sensation, friction and grip, and other aspects. The texture can optionally be non-abrasive to avoid compromising gloves worn by a user of the tool.

As shown in FIG. 7, the free ends of the members 652 include radially inward-facing wedge portions 636 similar to the wedge portions 336 described above in connection with the embodiment of FIGS. 3-5G. As discussed above, the wedge portions 636 include a narrow end 640. A width W of the narrow end 640 can be chosen to be narrow enough to enter a gap between the protective cover 210 and the exterior cover of the shaft 104, but wide enough that repeated use of the tool to remove the protective cover 210 does not quickly wear the narrow end 640 such that the width W widens significantly. As noted above, in one embodiment of the disclosure, a width W of about 0.015 inch (0.381 mm) provides an appropriate compromise between being narrow enough to enter the junction 107 (FIG. 5D) between the protective cover 210 and the exterior cover portion 105 to effectively remove the protective cover 210 and having sufficient durability for repeated use. In other embodiments, a suitable dimension for width W can vary from the exemplary dimension of 0.015 inches. For example, various factors such as the material of the members 652, the diameter of the instrument 100 and protective cover 210, the material of the protective cover 210, the size of a gap between the protective cover 210 and shaft exterior when the protective cover 210 is installed on the shaft 104, and the diameters of the various components of the shaft 104 can affect the appropriate dimension for W, and based on those various factors, an appropriate dimension for W can be greater or lesser than 0.015 inches.

Figure 8:
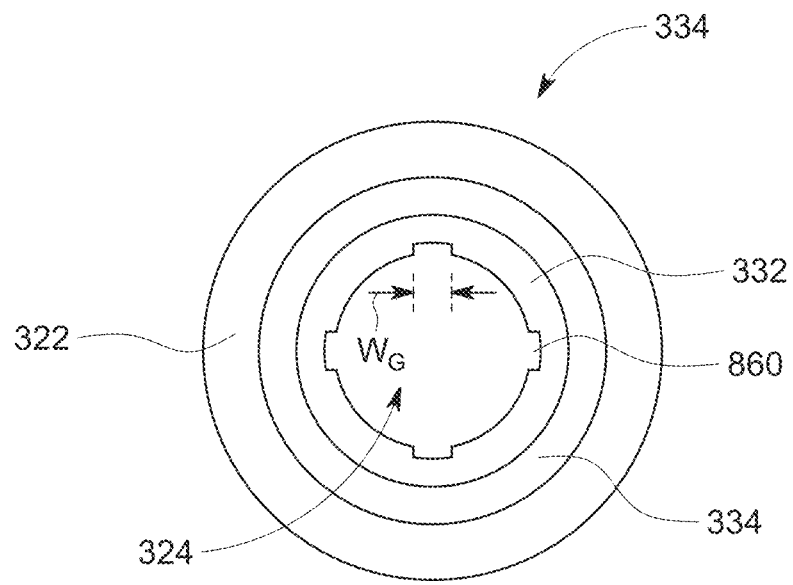
FIG. 8 is an end view of a portion of a protective cover installation and removal tool according to the present disclosure.

Various features can optionally be included in the resilient material insert 332 (FIG. 3) to alter the total force required to remove the protective cover 210 from the tool 316. For example, the resilient material insert 332 can optionally include one or more recessed portions on an interior surface of the resilient material insert. Referring now to FIG. 8, an end view of the first portion 334 of the embodiment of FIG. 3 is shown. Four longitudinal grooves 860 are shown formed in an interior surface in the resilient material insert 332, each groove 860 having a width WG. The longitudinal grooves 860 can be configured to provide the desired level of interference between the protective cover 210 and the resilient material insert 332. For example, in the absence of any longitudinal grooves, interference between the resilient material insert 332 and the protective cover 210 could potentially result in a force retaining the protective cover 210 within the tool 316 (FIG. 3) being greater than a force retaining the protective cover 210 on the instrument shaft 104. In such a situation, the tool 316 could not be removed from the protective cover 210 once the protective cover 210 is on the instrument shaft 104; rather, any attempt to remove the tool 316 would result in the protective cover 210 being removed from the shaft 104.

Providing the grooves 860 can reduce the interference force present between the protective cover 210 and the resilient material insert 332. For example, providing the grooves 860 can potentially relieve hoop stress present in the resilient material insert 332 when the protective cover 210 is inserted within the tool 316, thereby permitting greater deformation of the resilient material insert 332 and reducing the interference force retaining the protective cover 210 within the resilient material insert 332.

Additionally, presence of the grooves 860 reduces the total area of surface contact between the protective cover 210 and the resilient material insert 332, and thereby potentially reduces the total frictional force present between the protective cover 210 and the resilient material insert 332. Furthermore, the grooves 860 can enable trapped air or other fluids to be released from the tool 316 as the protective cover 210 is inserted within the tool 316.

Thus, the amount of total force required to remove the protective cover 210 from the tool 316 can be changed by changing the width WG and number of the longitudinal grooves 860. Increasing the width WG, and increasing the number of longitudinal grooves 860, both tend to reduce the total force required to remove the protective cover 210 from the tool 316. The present disclosure contemplates fewer than, or more than, four longitudinal grooves 860. For example, in other embodiments, the resilient material insert 332 can optionally include eight longitudinal grooves 860, ten, twelve, or more longitudinal grooves 860, odd numbers of longitudinal grooves, and other permutations or configurations. While the grooves 860 are longitudinal in the embodiment shown in FIGS. 3, 4, and 7, other configurations and features are within the scope of the disclosure. For example, the grooves can be helical, circumferential, and can optionally extend only partway along a length of the resilient material insert 332.

The configuration and number of the grooves 860 can be chosen based on the shape of the shaft 104 and desired interaction characteristics of the shaft 104 with the resilient material insert 332. For example, in some embodiments, the shaft 104 (FIG. 1) and/or protective cover 210 can have a non-circular cross section along the longitudinal axis of the shaft 104, such as an ovoid cross section with major and minor radial axes. In these embodiments, if the pattern of grooves were to exhibit radial symmetry, such as an even number of equally spaced grooves, the major axis of the shaft 104 could potentially align with diametrically opposite grooves. In this orientation, the resilient material insert 332 would not fit as tightly on the protective cover 210 compared to a configuration in which the major axis of the shaft 104 is not aligned with opposite grooves. Thus, the number of grooves can be chosen to be an odd number such that the cross section of the resilient material insert 332 does not exhibit radial symmetry and the pressure exerted by the resilient material insert 332 is consistent for different relative orientations of the protective cover 210 and shaft 104 in the resilient material insert 332.

Figure 11:
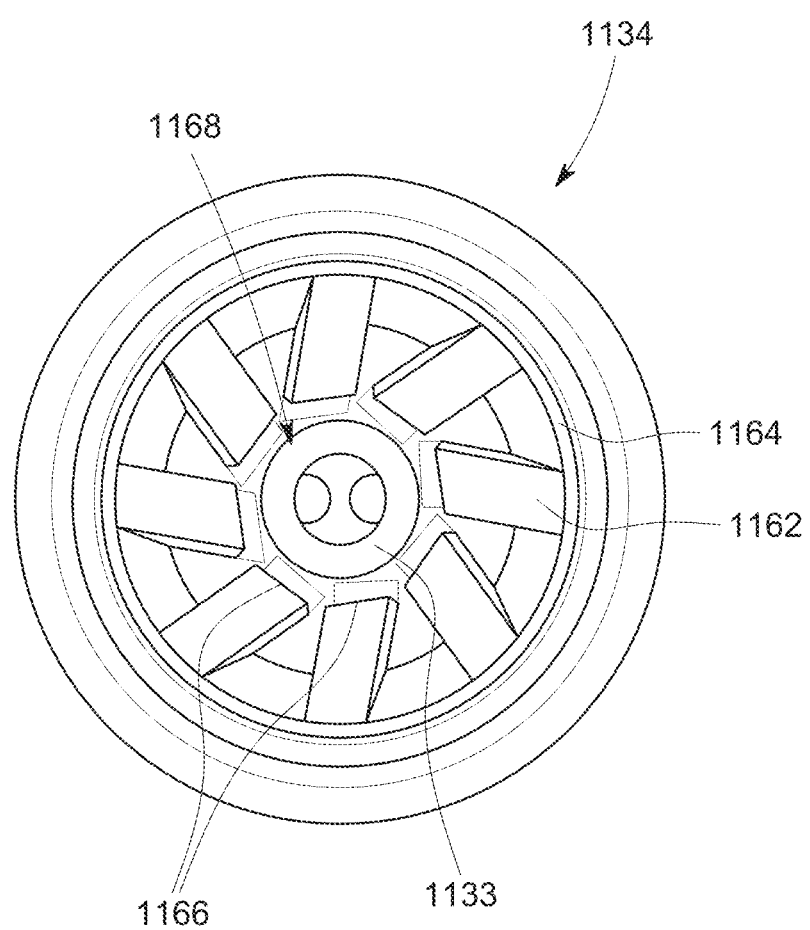
FIG. 11 is an end view of a portion of another protective cover installation and removal tool according to the present disclosure.

Turning to FIG. 11, an end view of a first portion 1134 of another tool according to the disclosure is shown. The first portion 1134 includes an interior portion 1133 that accepts a protective cover as discussed above. The interior portion 1133 includes a plurality of spokes 1162 extending from a periphery 1164 of the interior portion 1133. Distal ends 1166 of each of the spokes 1162 together generally form a bore into 1168 which a protective cover can be received. The spokes 1162 can flex as the protective cover is received in the interior portion 1133 to grip the protective cover and retain the protective cover within the interior portion 1133. While the tool according to FIG. 11 includes eight spokes, other numbers of spokes, such as less than eight or more than eight spokes, are considered within the scope of the disclosure.

Figure 12:
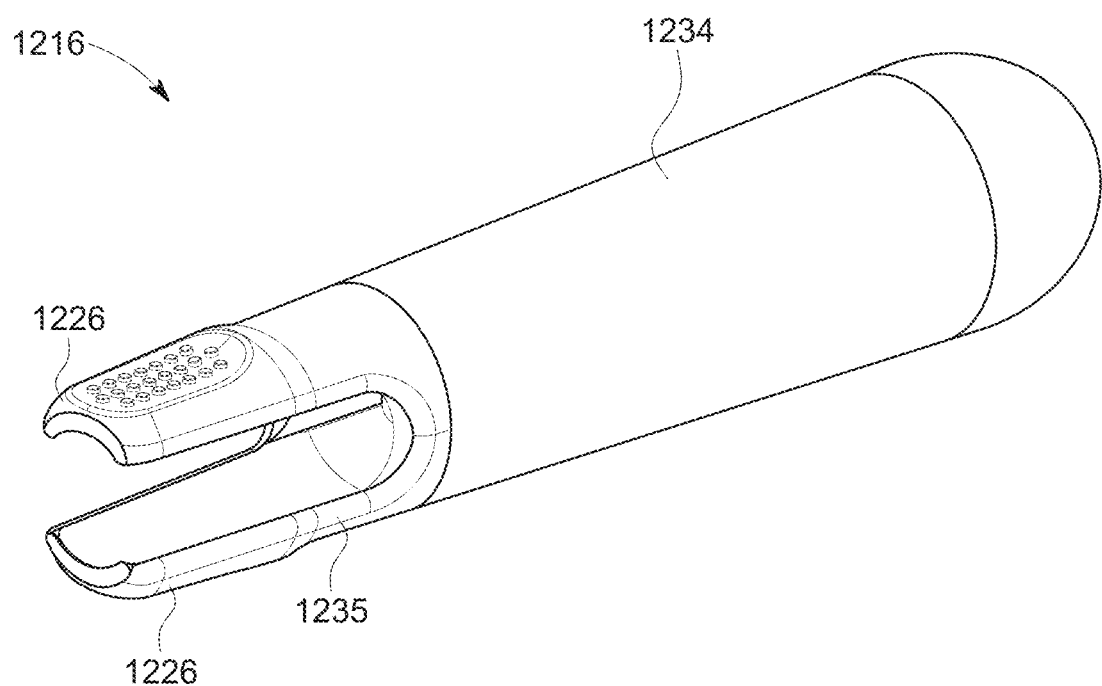
FIG. 12 is a perspective view of another protective cover installation and removal tool according to an embodiment of the present disclosure.

Referring now to FIG. 12, another embodiment of a protective cover installation and removal tool 1216 is shown. The protective cover installation and removal tool 1216 includes a first portion 1234 and a second portion 1235, similar to the configuration of the embodiment of FIGS. 3 and 4. The first portion 1234 comprises an interior passage 1224 configured to accept a protective cover, such as protective cover 210 shown in FIG. 2, and the second portion 1235 comprises two members 1226, similar to the members 326 discussed above in connection with the embodiment of FIGS. 3-5G.

Figure 13:
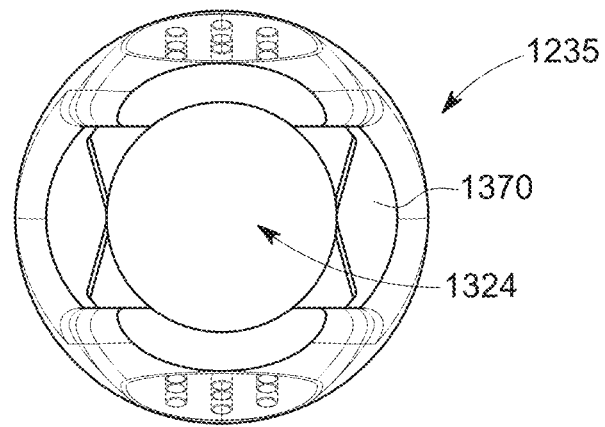
FIG. 13 is an end view of a portion of the protective cover installation and removal tool according to the embodiment of FIG. 12.

Referring now to FIG. 13, the second portion 1235 of the protective cover installation and removal tool 1216 of FIG. 12 is shown alone. The second portion 1235 comprises an interior passage 1324 that, when assembled with the second portion 1235 (FIG. 12), forms a continuous interion passage that accepts a protective cover. The second portion 1235 includes protrusions 1370 that extend radially inward to retain an inner portion within the second portion 1235 when the components are assembled, as discussed in further detail below.

Figure 14:
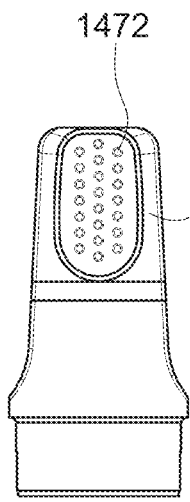
FIG. 14 is a front view of the portion of the protective cover installation and removal tool shown in FIG. 13.
Figure 15:
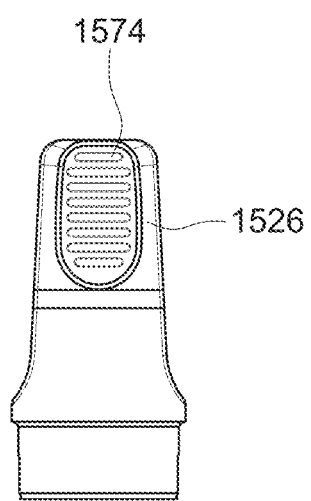
FIG. 15 is a front view of a portion of another embodiment of a protective cover installation and removal tool according to the present disclosure.

FIGS. 14 and 15 show exemplary embodiments of a second portion (e.g., corresponding to second portion 1235 shown in FIG. 12) with different configurations of tactile features configured to improve a user's grip on the protective cover installation and removal tool 1216. In the embodiment of FIG. 14, members 1426 comprise a pattern of raised dots 1472 configured to generate friction with a user's hand to improve a user's grip on the members 1426. In FIG. 15, members 1526 comprise a pattern of raised lines 1574 that similarly generate friction to improve a user's grip on the members 1526. The raised lines may be simpler and thus less costly to manufacture, while the dots may provide improved unidirectional grip.

Figure 16:
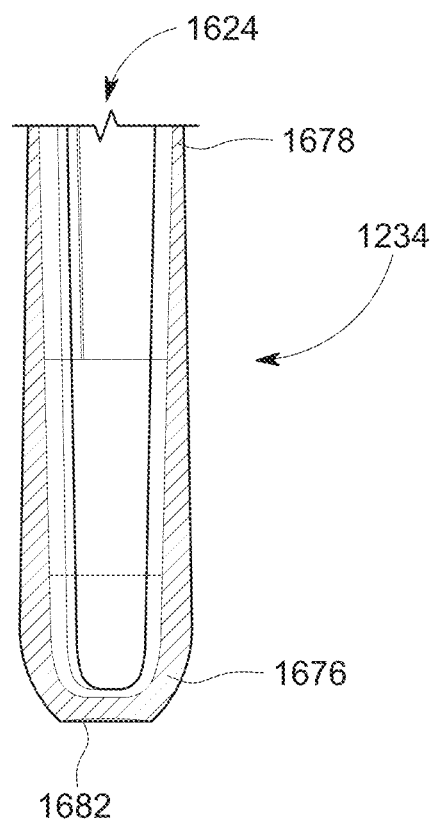
FIG. 16 is a cross-sectional view of an outer body portion of a protective cover installation and removal tool according to the embodiment of FIG. 12.

Referring now to FIG. 16, the first portion 1234 of the protective cover installation and removal tool 1216 of FIG. 12 is shown alone in cross-section. The first portion 1234 has an interior passage 1624 and a closed end 1676. The interior passage 1624 tapers from an open end 1678 of the first portion 1234 to the closed end 1676 of the first portion 1234. The first portion 1234 has a flat portion 1682 on the closed end on which the user can press or rest their thumb when installing the protective cover using the installation and removal tool 1216.

Figure 17:
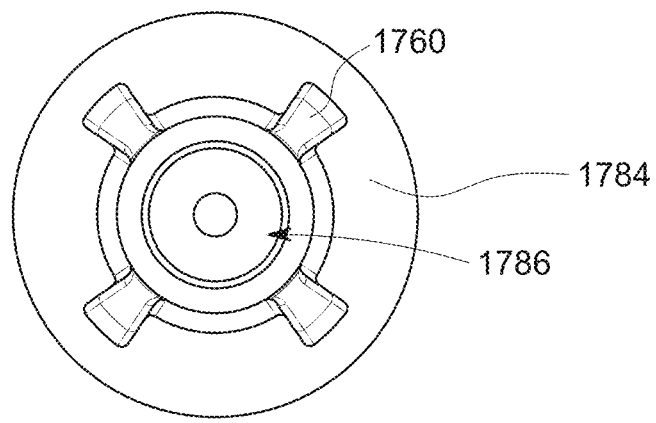
FIG. 17 is an end view of an inner portion of a protective cover installation and removal tool according to the embodiment of FIG. 12.
Figure 18:
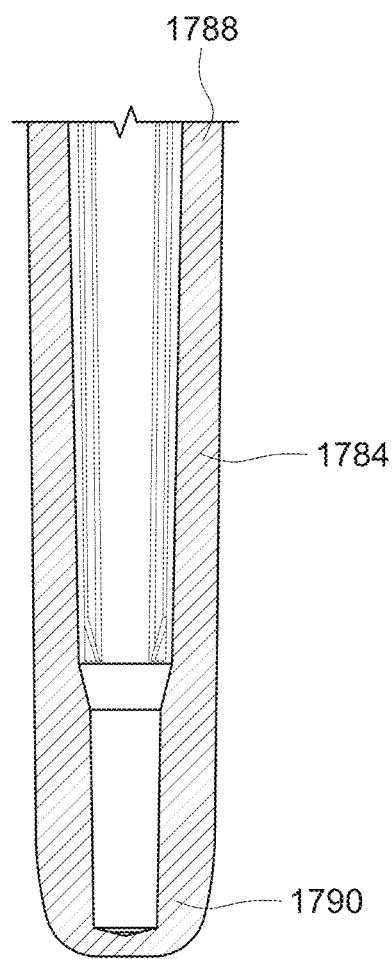
FIG. 18 is a cross-sectional view of the inner portion of the protective cover installation and removal tool according to the embodiment of FIG. 12.

The interior passage 1624 is configured to accept a resilient material insert, such as the resilient material insert 1784 shown in FIGS. 17 and 18. FIG. 17 shows an end view of resilient material insert 1784. The resilient material insert 1784 has an interior passage 1786 with longitudinal grooves 1760 that extend along a portion of the length of the interior passage 1786. Referring to FIG. 18, a side cross-sectional view of the resilient material insert 1784 is shown. Similar to the configuration of the first portion 1234, the resilient material insert 1784 tapers slightly from an open end 1788 to a closed end 1790.

The degree of taper of the interior of the first portion 1234 can optionally be greater than the degree of taper of the exterior of the resilient material insert 1784 along at least a portion of the length of the first portion 1234 and the resilient material insert 1784. In some embodiments, a tapered clearance can exist between the outer surface of the resilient material insert 1784 and the inner surface of the first portion 1234.

Figures 19, 20:
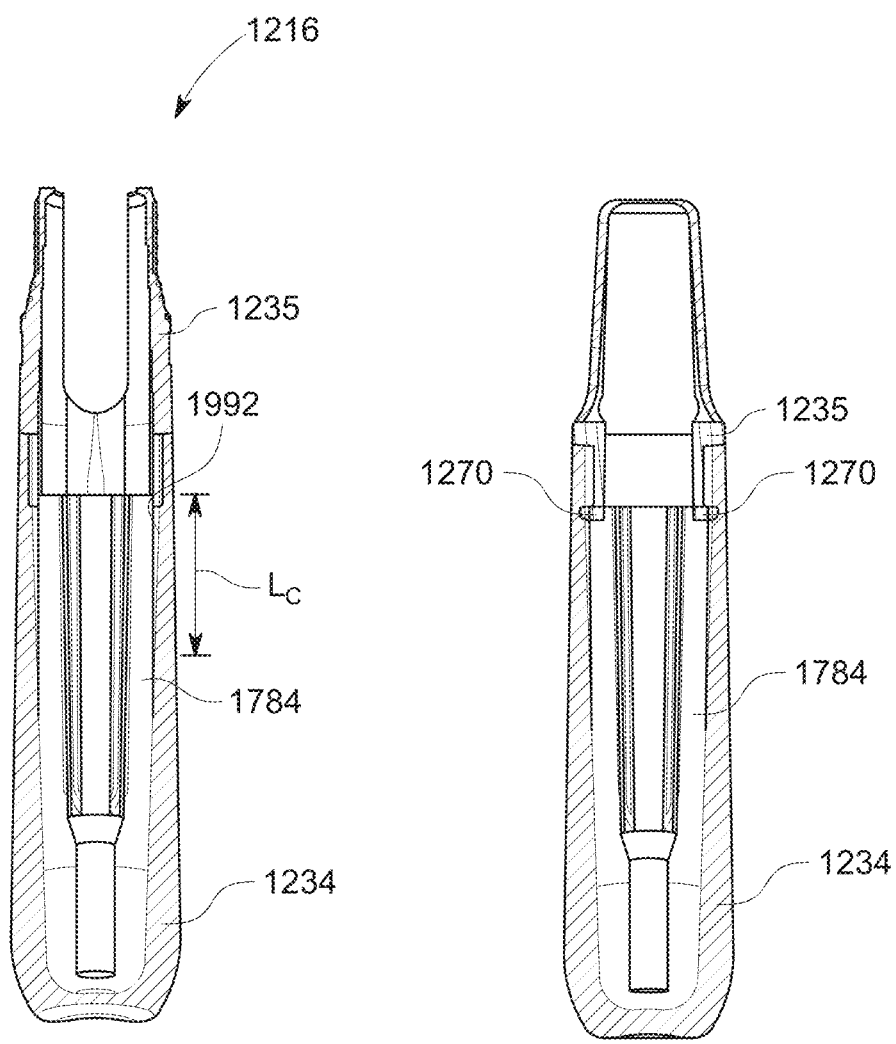
FIG. 19 is a side cross-sectional view of the protective cover installation and removal tool according to the embodiment of FIG. 12.
FIG. 20 is a front cross-sectional view of the protective cover installation and removal tool according to the embodiment of FIG. 12.
Figure 21:
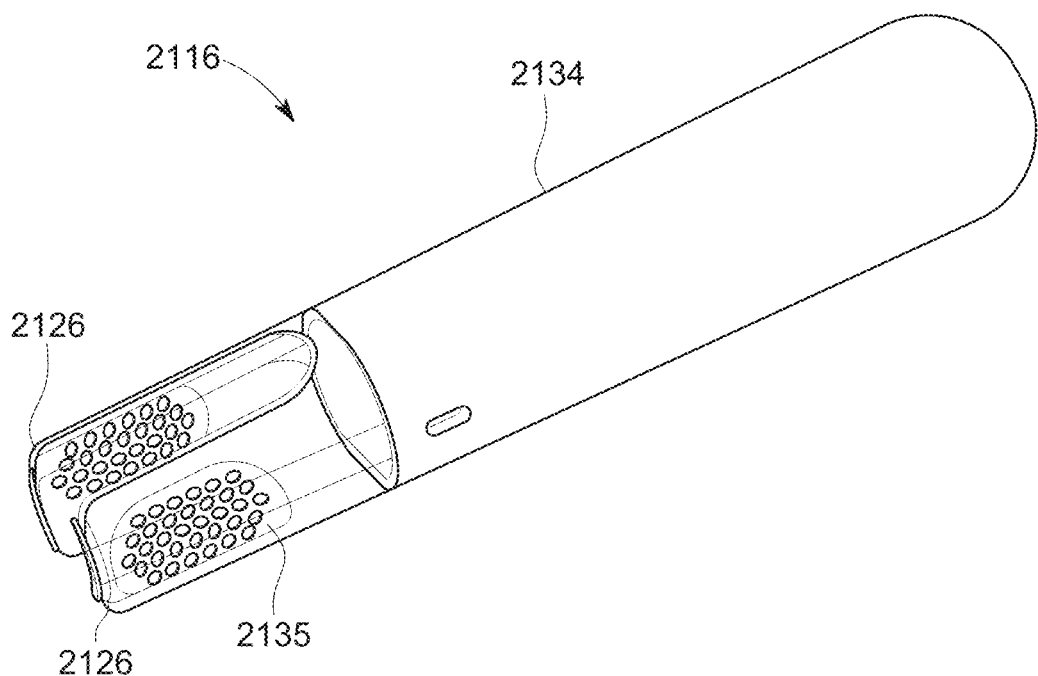
FIG. 21 is a perspective view of another embodiment of a protective cover removal and installation tool according to an exemplary embodiment of the present disclosure.

For example, referring now to FIG. 19, the protective cover installation and removal tool 1216 shown in FIG. 12 is shown in side cross-sectional view, with the resilient material insert 1784 installed within the first portion 1234, and the second portion 1235 installed within the first portion 1234. A clearance 1992 exists between the resilient material insert 1784 and the first portion 1234 along a portion $L_C$ of the length of the installation and removal tool 1216. The clearance 1992 can facilitate initial insertion of the protective cover (e.g., the protective cover 210 shown in FIG. 2) within the installation and removal tool 1216 by enabling the resilient material insert 1784 to stretch as the protective cover is inserted. As the protective cover is inserted into the resilient material insert 1784 further, i.e., beyond the portion Lc, the protective cover enters a portion of the resilient material insert that is in contact with, and restrained by, the first portion 1234, thereby providing a tight grip on the protective cover for installation. The clearance 1992 can be expressed as a diametral clearance (i.e., a difference in diameters) between the resilient material insert 1784 and the first portion 1234 and can range, for example and not limitation, from about 0.01" (0.254 mm) to about 0.05" (1.27 mm). In an exemplary embodiment, the clearance 1992 can be about 0.02" (0.508 mm) to about 0.03" (0.762 mm).

As noted in connection with the description of FIG. 13, the second portion 1235 of the protective cover installation and removal tool 1216 includes protrusions 1270. As shown in FIG. 20, the protrusions 1270 contact the resilient material insert 1784 with an interference fit and retain the resilient material insert 1784 within the first portion 1234 of the installation and removal tool 1216, e.g., when the user removes the installation and removal tool 1216 from the protective cover after installing the protective cover over the instrument. The interference fit between the resilient material insert 1784 and the second portion 1235 also functions to center the resilient material insert 1784 within the first portion 1232 when the second portion 1235 is installed within the first portion 1234. As with other embodiments described above, the second portion 1235 is retained in the first portion 1234 by an interference fit between the second portion 1235 and the first portion 1234.

FIGS. 21-26 show various views and components of a protective cover installation and removal tool 2116 according to yet another exemplary embodiment of the present disclosure. The tool 2116 includes a first portion 2134 with an interior passage dimensioned to receive a resilient material insert 2184 (see FIG. 22). The interior passage can be, for example, in a range of from less than 1 inch (25.4 mm) to 2 inches (50.8 mm) or more. The resilient material insert 2184 is configured to receive a protective cover (such as protective cover 210 shown in FIG. 2). A second portion 2135 is coupled with the first portion 2134. The second portion 2135 includes members 2126 disposed at a distal portion configured to be gripped by a user, as discussed in connection with other exemplary embodiments herein.

Figure 22:
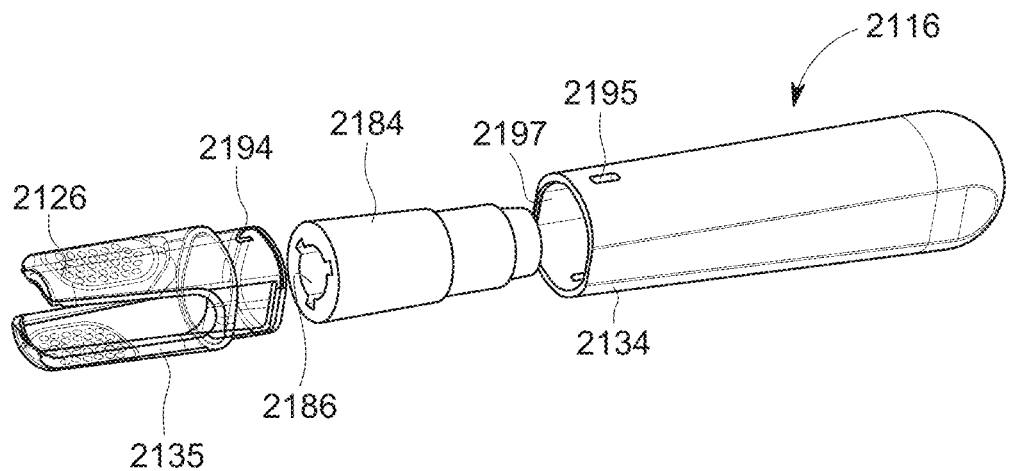
FIG. 22 is an exploded perspective view of the protective cover removal and installation tool of FIG. 21.

Referring now to FIG. 22, the protective cover installation and removal tool 2116 is shown in an exploded view, revealing the resilient material insert 2184 that fits within the first portion 2134. The resilient material insert 2184 includes an interior passage 2186. The resilient material insert 2184 can comprise a material such as silicone rubber or other resilient material, as discussed above. The second portion 2135 can be retained within the first portion 2134 by an interference fit, as discussed above. Further, the first portion 2134 and the second portion 2135 can include complementary retaining features configured to retain the second portion 2135 within the first portion 2134. Such complementary features can be in addition to, or in place of, the interference fit. Stated differently, the second portion 2135 can be retained in the first portion 2134 by the complementary retaining features alone, or by an interference fit between the first portion 2134 and second portion 2135 in addition to the complementary retaining features.

With continued reference to FIG. 22, the complementary retaining features can include one or more projections 2194 of the second portion 2135 configured to be received by one or more apertures 2195 of the first portion 2134. In an assembled state of the first portion 2134 and the second portion 2135, the one or more projections 2194 of the second portion 2135 engage within the one or more apertures 2195 to retain the second portion 2135 and the first portion 2134 together. It will be appreciated by one of ordinary skill in the art that the locations of the projections 2194 and apertures 2195 could be changed from the configuration shown in FIG. 22, such as the projections 2194 being part of the first portion 2134 and the apertures 2195 being part of the second portion 2135. In addition, the number of complementary retaining features may vary from one to more than one and can be placed in various locations around an inner circumferential surface of the first portion and an outer circumferential surface of the second portion.

Figure 23:
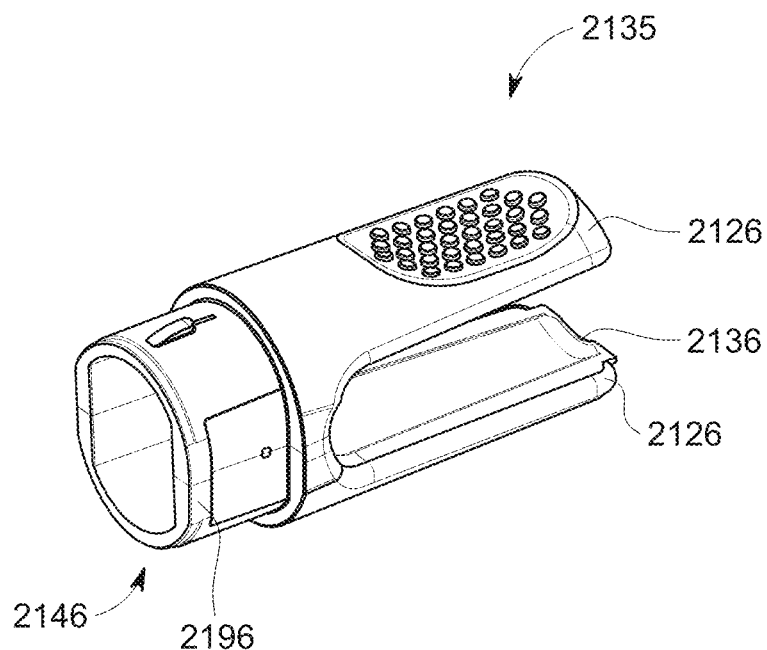
FIG. 23 is a perspective view of a portion of the protective cover removal and installation tool of FIG. 21.

Referring now to FIGS. 22 and 23, the second portion 2135 is shown in isolation. The second portion 2135 includes an extension 2146 configured to be received within the interior passage of the first portion 2134. The extension 2146 can optionally include registration surfaces 2196 that interface with corresponding surfaces 2197 on the first portion 2134 to orient the first portion 2134 and second portion 2135 relative to one another when assembled. Other orienting features, such as splines, keys, flats, etc., can optionally be used in addition to, or in place of, the registration surfaces 2196 and corresponding surfaces 2197. Members 2126 include wedge-shaped portions 2136 as discussed in detail in connection with the embodiments of at least FIGS. 2-7.

Figure 24:
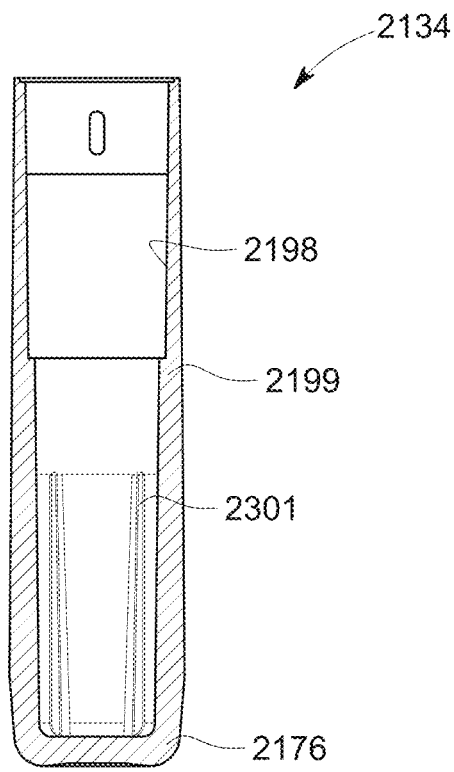
FIG. 24 is a cross-sectional side view of a body portion of the protective cover removal and installation tool shown in FIG. 21.

According to some embodiments of the present disclosure, the first portion 2134 includes features that position the resilient material insert 2184 longitudinally within the first portion 2134. For example, the interior passage can have a stepped surface profile with one or more step features that define changes in diameter of the interior passage. With reference to FIG. 24, the first portion 2134 is shown in a cross-sectional side view. The interior passage of the first portion 2134 defines an inner lateral sidewall 2198. In the embodiment of FIG. 24, the profile of the inner lateral sidewall 2198 features a step feature 2199. The step feature 2199 is configured to interact with features of the resilient material insert 2184 to maintain a longitudinal position of the resilient material insert 2184 relative to the first portion 2134. The first portion 2134 also includes a plurality of longitudinally extending ribs 2301 within the interior passage at a closed end 2176 of the first portion 2134.

Figure 25A:
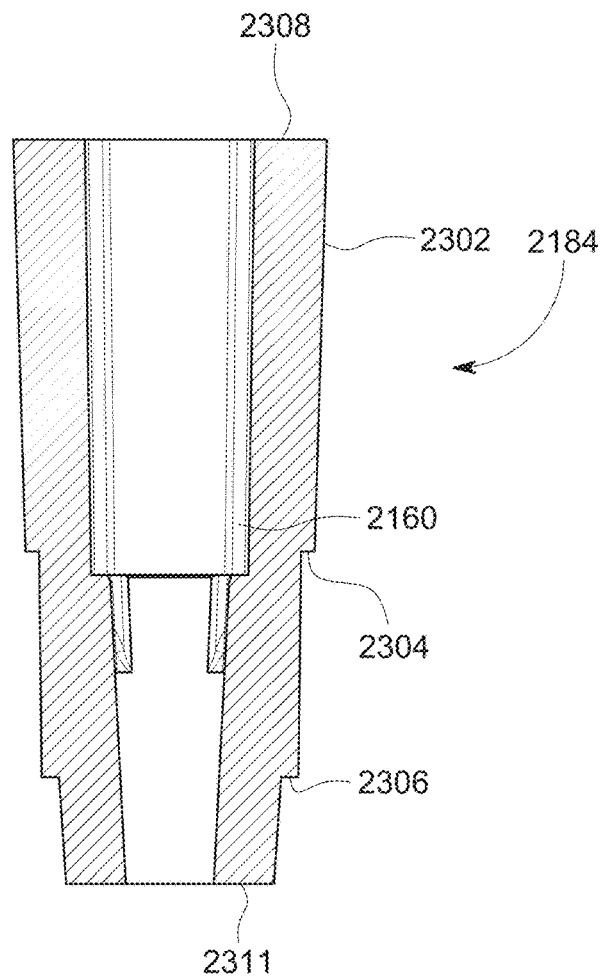
FIG. 25A is a cross-sectional side view of the inner portion shown in FIG. 25A.

With reference now to FIG. 25A, which shows a cross-sectional side view of the resilient material insert 2184, the resilient material insert 2184 has an outer lateral sidewall 2302 having a stepped surface profile with a first step feature 2304 and a second step feature 2306. The outer lateral sidewall 2302 gradually tapers between the first and second step features 2304 and 2306 and from a first end 2308 to a second end 2311 of the resilient material insert 2184.

Figure 25B:
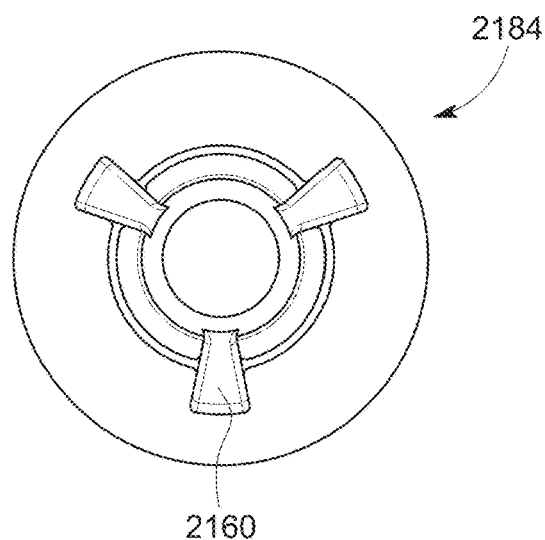
FIG. 25B is an end view of an inner portion of the protective cover installation and removal tool of FIG. 21.

FIG. 25B shows an end view of the resilient material insert 2184. The resilient material insert 2184 includes an internal surface with a plurality of longitudinally extending grooves 2160. In the tool of FIGS. 21-26, the resilient material insert 2184 includes three equally-spaced longitudinally extending grooves 2160. As discussed above, the odd number of grooves 2160 provides a non-symmetrical cross section of the resilient material insert 2184, and thereby can provide a consistent tightness of fit for shafts and covers having symmetrical, ovoid cross sections. As discussed above in connection with FIGS. 8 and 11, different numbers and configurations of longitudinal grooves are within the scope of the disclosure, depending on various factors such as the desired frictional force between a protective cover used with the installation and removal tool and material characteristics of the resilient material insert 2184. As a non-limiting example, in the embodiment of FIGS. 21-26, the resilient material insert comprises silicone rubber material exhibiting a durometer measurement of Shore 40 A. In other embodiments, the durometer measurement can be less than or more than Shore 40 A, such as, for example, in a range of from Shore 20 A to Shore 75 A, or a different range or lesser or greater durometer values. The three longitudinal grooves 2160 provide the desired interface characteristics between the protective cover and the installation and removal tool. As shown in the cross-sectional view of FIG. 25A, the longitudinal grooves 2160 extend from the first end 2308 of the resilient material insert to a longitudinal location on the resilient material insert 2184 intermediate the first step feature 2304 and the second step feature 2306. When inserted within the resilient material insert 2184, a distal end of a protective cover can be positioned longitudinally beyond the longitudinal grooves 2160, and the solid circumference of the resilient material insert 2184 can support the end of the protective cover and transmit sufficient force to the protective cover to install the protective cover over the instrument.

Figure 26:
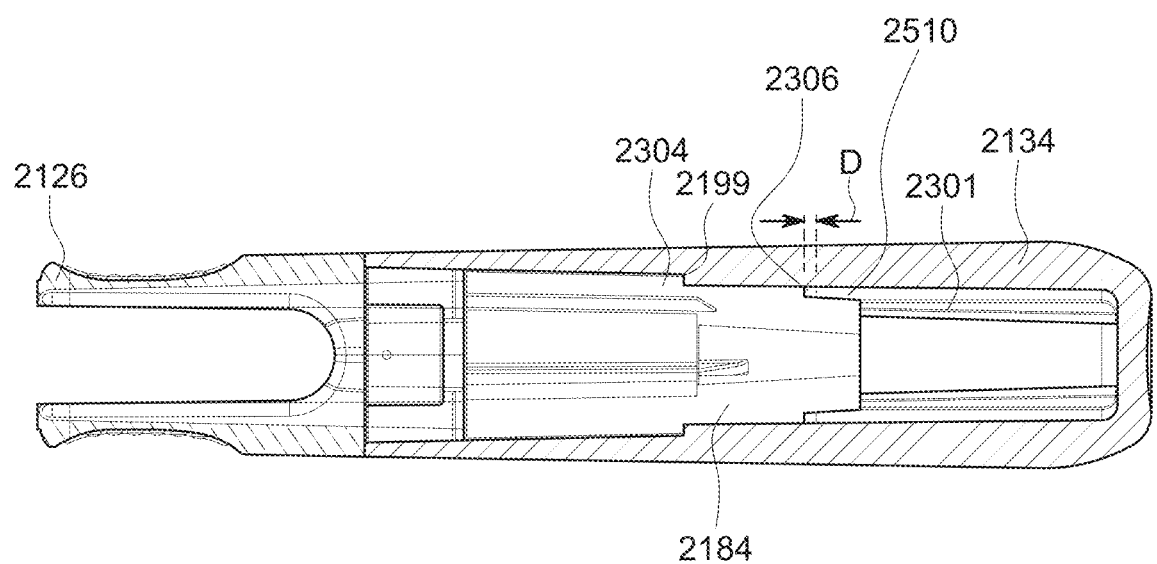
FIG. 26 is a longitudinal cross-sectional view of the protective cover installation and removal tool of FIG. 21.

Referring now to FIG. 26, a cross-sectional view of the assembled protective cover installation and removal tool 2116 according to FIGS. 21-24 is shown. In the assembled state, the first step feature 2304 of the resilient material insert 2184 rests against the step feature 2199 of the first portion 2134 and defines a longitudinal position of the resilient material insert 2184 relative to the first portion 2134. The second step feature 2306 of the resilient material insert 2184 is longitudinally spaced from a terminal end 2510 of each of the ribs 2301 by a distance D, which can be, for example, in a range of from 0 to 0.1 inches (2.54 mm). In the tool of FIG. 26, the distance D is approximately 0.05 inch (1.27 mm). This spacing enables the resilient material insert 2184 to flex and expand around a protective cover when the protective cover is inserted in the resilient material insert 2184 while preventing bunching of the resilient material. In addition, if the first step feature 2304 of the resilient material insert 2184 slips past the step feature 2199 of the first portion 2134, the second step feature 2306 of the resilient material insert 2184 bottoms out against the ribs 2301 and prevents the resilient material insert 2184 from being forced further into the first portion 2134.

Figure 9:
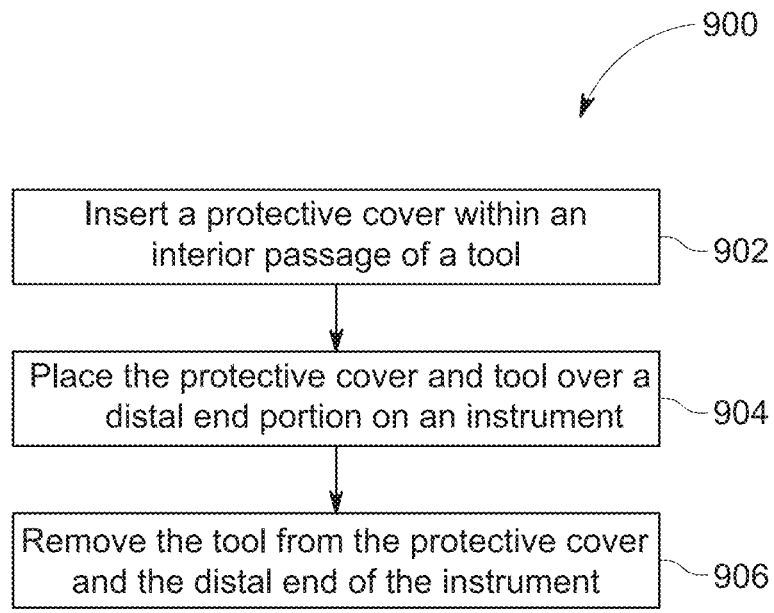
FIG. 9 is a flow chart of a work flow for installing a protective cover using a protective cover installation and removal tool of the present disclosure.

Referring now to FIG. 9, an exemplary workflow 900 for installing a protective cover on an instrument is shown. At 902, a protective cover is inserted within an interior passage of a tool. At 904, the protective cover and tool are placed over a distal end portion of an instrument. At 906, the tool is removed from the protective cover and the distal end portion of the instrument, and the protective cover remains in place over the distal end portion of the instrument, e.g., for use during a procedure.

Figure 10:
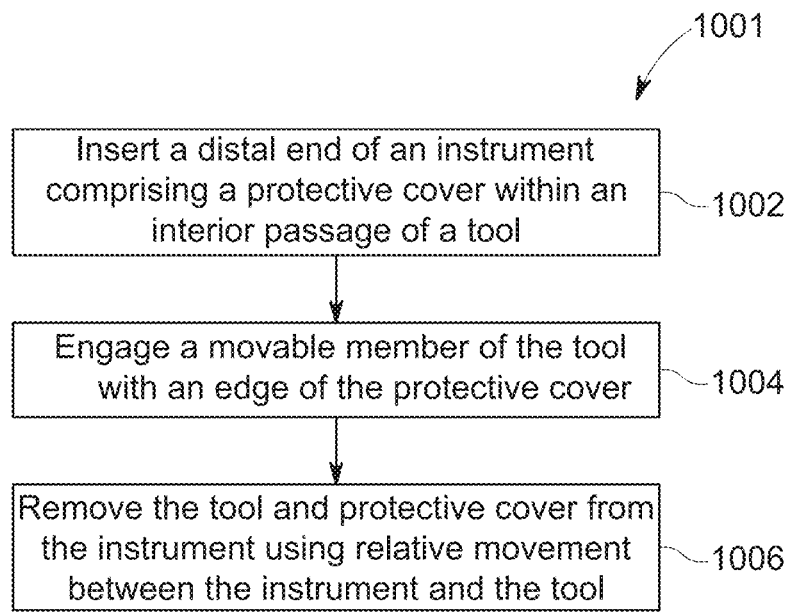
FIG. 10 is a flow chart of a work flow for removing a protective cover using a protective cover installation and removal tool of the present disclosure.

Referring now to FIG. 10, an exemplary workflow 1001 for removing a protective cover from an instrument is shown. The workflow 1001 includes inserting a distal end of an instrument comprising a protective cover within an interior passage of a tool at 1002. At 1004, an edge of the protective cover is engaged with a movable member of the tool. At 1006, relative movement between the instrument and the tool removes the protective cover from the instrument.

Embodiments of the disclosure provide tools that facilitate installation and removal of protective covers on instruments, such as surgical instruments. Tools and instruments including the embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture," U.S. Pat. No. 9,295,524 (filed May 31, 2018) to Schena et al., entitled "Redundant Axis and Degree of Freedom for Hardware-Constrained Remote Center Robotic Manipulator," and U.S. Pat. No. 8,852,208 (filed Aug. 12, 2010) to Gomez et al., entitled "Surgical System Instrument Mounting," each of which is hereby incorporated by reference in its entirety. Further, the embodiments described herein may be used, for example, with a da Vinci® Surgical System, such as the da Vinci Si® Surgical System (model no. IS3000) or the da Vinci Xi® Surgical System, both with or without Single-Site® single orifice surgery technology, all commercialized by Intuitive Surgical, Inc. of Sunnyvale, California. Although various embodiments described herein are discussed with regard to surgical instruments used with a manipulating system of a teleoperated surgical system, the present disclosure is not limited to use with surgical instruments for a teleoperated surgical system. For example, various embodiments described herein can optionally be used in conjunction with hand-held, manual surgical instruments, or other surgical and non-surgical tools.

Figure 27:
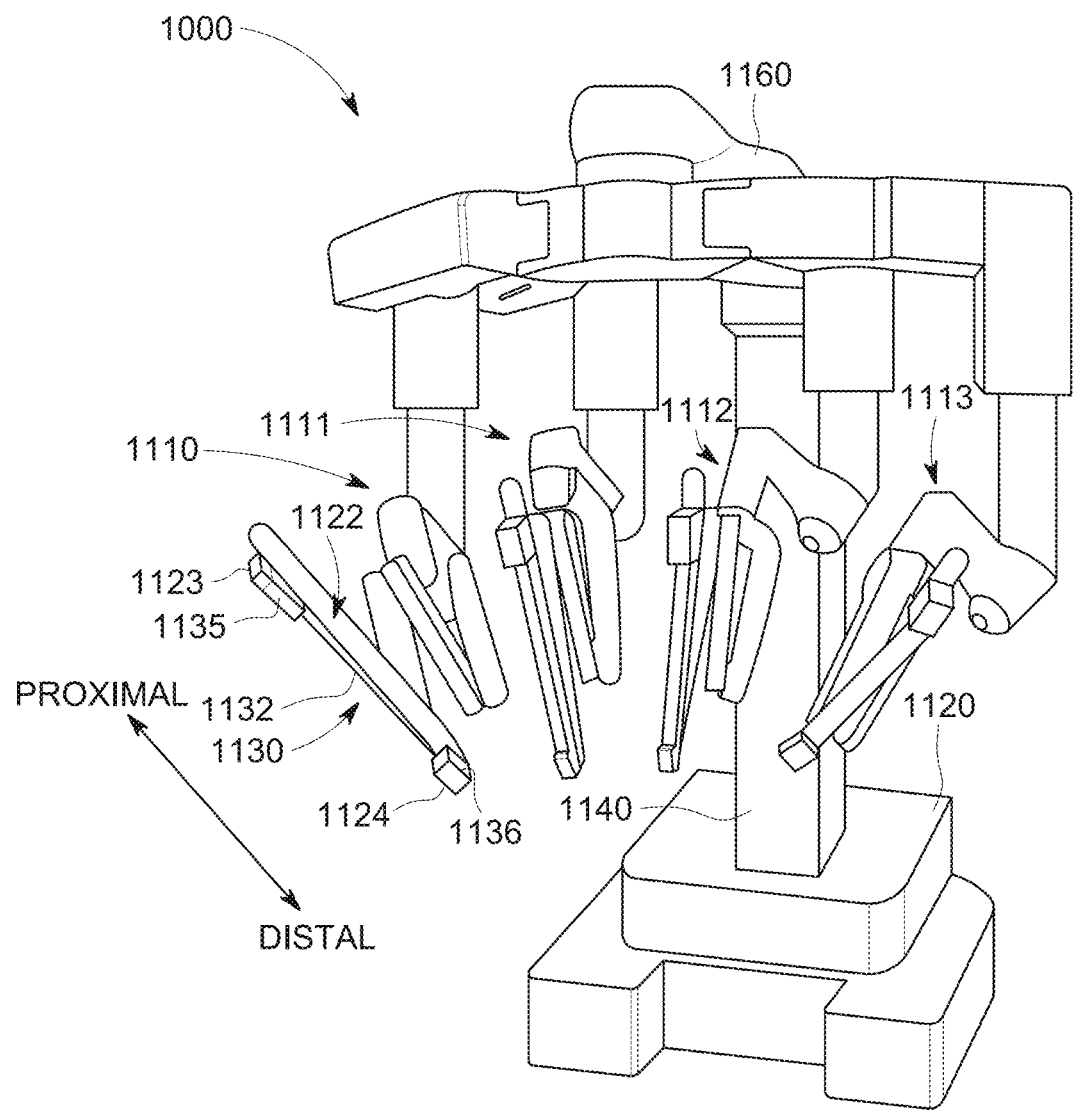
FIG. 27 is a perspective view of a manipulating system according to the present disclosure.

As discussed above, in accordance with various embodiments, surgical instruments of the present disclosure are configured for use in teleoperated, computer-assisted surgical systems (sometimes referred to as robotic surgical systems). Referring now to FIG. 27, an embodiment of a manipulating system 1100 of a teleoperated, computer-assisted surgical system, to which surgical instruments are configured to be mounted for use, is shown. Such a surgical system may further include a surgeon console (not shown) for receiving input from a user to control instruments of manipulating system 1100, as well as an auxiliary system, such as a control/vision cart (not shown), as described in, for example, U.S. Pat. Nos. 9,358,074 and 9,295,524, incorporated above.

As shown in the embodiment of FIG. 27, a manipulating system 1100 includes a base 1120, a main column 1140, and a main boom 1160 connected to main column 1140. Manipulating system 1100 also includes a plurality of arms 1110, 1111, 1112, 1113, which are each connected to main boom 1160. Arms 1110, 1111, 1112, 1113 each include an instrument mount portion 1122 to which an instrument 1130 may be mounted, which is illustrated as being attached to arm 1110. Portions of arms 1110, 1111, 1112, 1113 may be manipulated during a surgical procedure according to commands provided by a user at the surgeon console. In an embodiment, signal(s) or input(s) transmitted from a surgeon console are transmitted to the control/vision cart, which may interpret the input(s) and generate command(s) or output(s) to be transmitted to the manipulating system 1100 to cause manipulation of an instrument 1130 (only one such instrument being mounted in FIG. 27) and/or portions of arm 1110 to which the instrument 1130 is coupled at the manipulating system 1100.

Instrument mount portion 1122 comprises a drive assembly 1123 and a cannula mount 1124, with a force transmission mechanism 1135 of the instrument 1130 connecting with the drive assembly 1123, according to an embodiment. Cannula mount 1124 is configured to hold a cannula 1136 through which a shaft 1132 of instrument 1130 may extend to a surgery site during a surgical procedure. Drive assembly 1123 contains a variety of drive and other mechanisms that are controlled to respond to input commands at the surgeon console and transmit forces to the force transmission mechanism 1135 to actuate the instrument 1130, as those skilled in the art are familiar with.

Although the embodiment of FIG. 27 shows an instrument 1130 attached to only arm 1110 for ease of viewing, an instrument may be attached to any and each of arms 1110, 1111, 1112, 1113. An instrument 1130 may be a surgical instrument with an end effector as discussed herein. A surgical instrument with an end effector may be attached to and used with any of arms 1110, 1111, 1112, 1113. The embodiments described herein are not limited to the embodiment of FIG. 27 and various other teleoperated, computer-assisted surgical system configurations may be used with the embodiments described herein.

Figure 28:
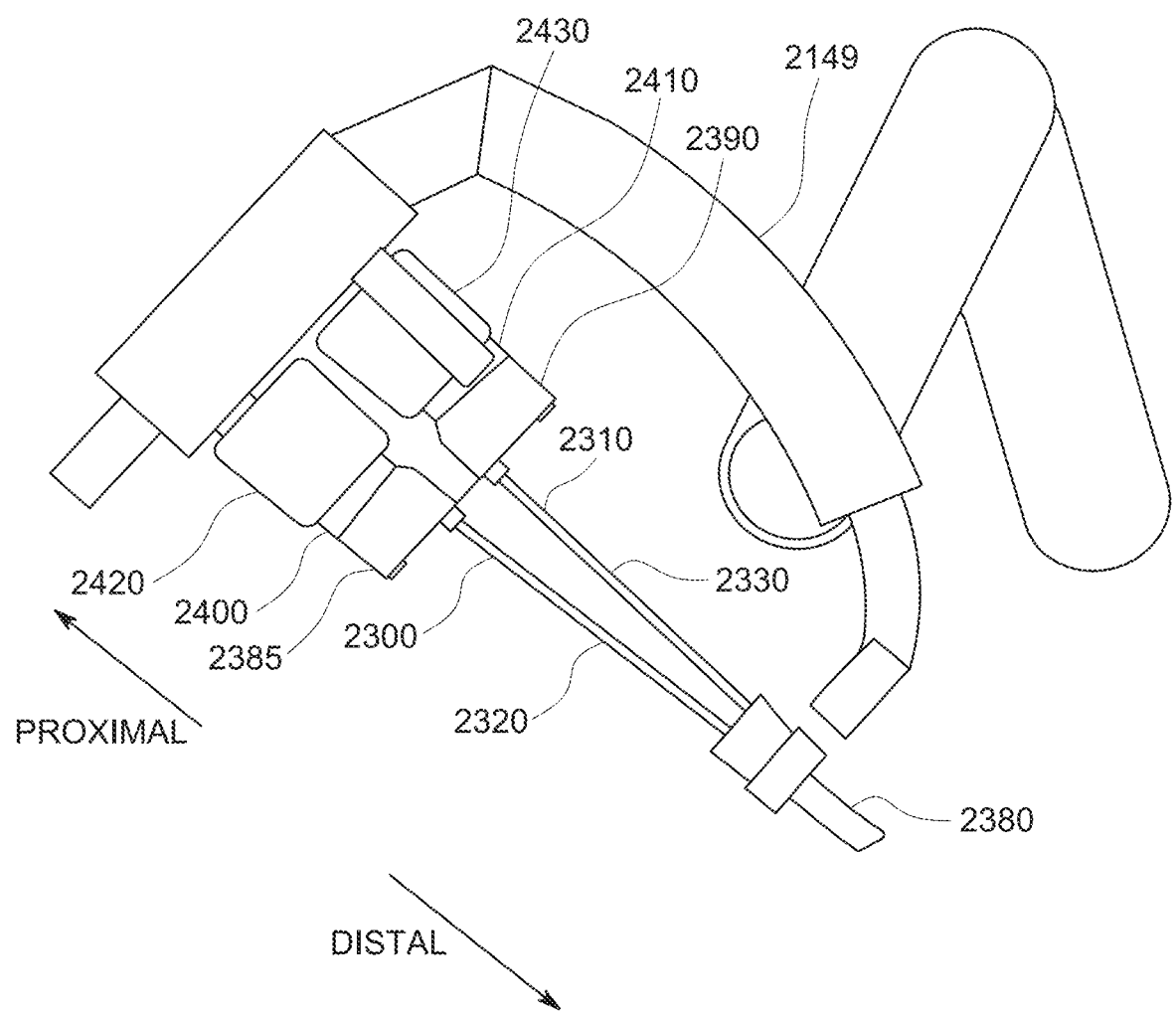
FIG. 28 is a partial schematic view of a manipulator arm of a manipulating system according to the present disclosure with two electrosurgical instruments in an installed position, one of which is shown in electrical communication with a flux generator.

Other configurations of surgical systems, such as surgical systems configured for single-port surgery, are also contemplated. For example, with reference now to FIG. 28, a portion of an embodiment of a manipulator arm 2140 of a manipulating system with two surgical instruments 2300, 2310 in an installed position is shown. A teleoperated robotic surgical system, including a manipulating system comprising manipulator arm 2140, may be configured according to the embodiments described in U.S. Patent App. Pub. No. US 2014/0128886 A1 (filed Nov. 1, 2013), to Holop et al. and titled "Flux disambiguation for teleoperated surgical systems," the disclosure of which is incorporated by reference herein. The schematic illustration of FIG. 28 depicts only two surgical instruments for simplicity, but more than two surgical instruments may be received in an installed position at a manipulating system as those having ordinary skill in the art are familiar with. Each surgical instrument 2300, 2310 includes an instrument shaft 2320, 2330 that at a distal end has a moveable end effector or an endoscope, camera, or other sensing device, and may or may not include a wrist mechanism (not shown) to control the movement of the distal end.

In the embodiment of FIG. 28, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site. Other configurations of manipulating systems that can be used in conjunction with the present disclosure can use several individual manipulator arms. In addition, individual manipulator arms may include a single instrument or a plurality of instruments. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 2385, 2390 are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate instruments 2300, 2310. The diameter or diameters of an instrument shaft, wrist mechanism, and end effector are generally selected according to the size of the cannula with which the instrument will be used and depending on the surgical procedures being performed. In various embodiments, a shaft and/or wrist mechanism has a diameter of about 4 mm, 5 mm, or 8 mm in diameter, for example, to match the sizes of some existing cannula systems.

This description and the accompanying drawings that illustrate embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A tool for installing and/or removing a protective cover of an instrument, comprising:
   a body portion having an open end and a closed end, the open end defining an interior passage that extends into the body portion along a longitudinal axis of the body portion toward the closed end of the body portion, the interior passage being configured to receive at least a portion of the protective cover in the interior passage, wherein the body portion further comprises a resilient material layer forming an outer surface of the body portion; and
   one or more members connected to the body portion, each of the one or more members comprising a free end movable relative to the body portion.

2. The tool of claim 1, further comprising
   at least one engaging portion at the free end of each of the one or more members.

3. The tool of claim 2, wherein the at least one engaging portion comprises at least one pincer element.

4. The tool of claim 3, wherein the at least one pincer element comprises a wedge-shaped projection.

5. The tool of claim 4, wherein the wedge-shaped projection comprises a narrow end having a width of less than 0.050 inches (1.27 mm).

6. The tool of claim 5, wherein the narrow end of the wedge-shaped projection has a width of about 0.015 inches (0.381 mm).

7. The tool of claim 1, wherein the one or more members extend away from the open end of the body portion along the longitudinal axis of the body portion.

8. The tool of claim 1, further comprising a resilient portion within the body portion, the resilient portion forming at least a portion of the interior passage.

9. The tool of claim 1, wherein the one or more members are coupled to the body portion by resilient hinge portions.

10. The tool of claim 1, wherein the one or more members are coupled to the body portion on opposite sides of the interior passage of the open end of the body portion.

11. The tool of claim 1, further comprising one or more recessed portions on an interior surface of the interior passage.

12. The tool of claim 11, wherein the one or more recessed portions comprise one or more longitudinal grooves on the interior surface of the interior passage.

13. The tool of claim 1, wherein each of the one or more members comprises a shoulder portion extending radially outward from a portion of each of the one or more members opposite the free end of each of the one or more members.

14. A tool for installing and/or removing a protective cover of an instrument, comprising:
   a body portion having an open end and a closed end, the open end defining an interior passage that extends into the body portion along a longitudinal axis of the body portion toward the closed end of the body portion, the interior passage being configured to receive at least a portion of the protective cover in the interior passage; and
   one or more members connected to the body portion, each of the one or more members comprising a free end movable relative to the body portion, wherein the one or more members each comprise a textured outer surface.

15. The tool of claim 14, wherein the textured outer surface comprises a pebbled texture.

16. A tool for installing and/or removing a protective cover of an instrument, comprising:
   a body portion having an open end and a closed end, wherein the body portion comprises:
      a first portion and a second portion coupled together, and
      a resilient insert positioned within the first portion, and wherein the open end defines an interior passage that extends into the body portion along a longitudinal axis of the body portion toward the closed end of the body portion, the interior passage is configured to receive at least a portion of the protective cover in the interior passage, and one or more members connected to the body portion, each of the one or more members comprising a free end movable relative to the body portion, wherein:

the interior passage is defined by an inner lateral sidewall of the first portion;

the inner lateral sidewall comprises a step feature;

the resilient insert comprises another step feature; and in an assembled state of the resilient material insert and the first portion, the another step feature of the resilient material insert engages the step feature of the inner lateral sidewall.

17. The tool of claim 16, wherein the second portion retains the resilient insert within the first portion when the second portion and first portion are coupled together.

18. The tool of claim 16, wherein the first portion comprises one or more ribs extending into the interior passage proximate the closed end of the body portion.

19. The tool of claim 16, wherein:

one of the first portion and the second portion comprises a projection;

the other of the first portion and the second portion comprises an aperture; and the aperture is configured to receive the projection in an assembled state of the first portion and the second portion.

\* \* \* \* \*